(12) United States Patent
Birtwhistle et al.

(10) Patent No.: US 9,549,324 B2
(45) Date of Patent: *Jan. 17, 2017

(54) COEXISTENCE OF MULTIPLE RADIOS IN A MEDICAL DEVICE

(71) Applicant: Roche Diabetes Care, Inc., Indianapolis, IN (US)

(72) Inventors: Daniel Birtwhistle, Fishers, IN (US); Thomas D. Gurley, Indianapolis, IN (US); Mark Nierzwick, Brownsburg, IN (US); Ulrich Porsch, Weinheim (DE); John F. Price, McCordsville, IN (US); Blaine E. Ramey, Indianapolis, IN (US); Raymond Strickland, Indianapolis, IN (US)

(73) Assignee: ROCHE DIABETES CARE, INC., Indianapolis, IN (US)

(*) Notice: Subject to any disclaimer, the term of this patent is extended or adjusted under 35 U.S.C. 154(b) by 329 days.

This patent is subject to a terminal disclaimer.

(21) Appl. No.: 14/163,510

(22) Filed: Jan. 24, 2014

(65) Prior Publication Data

US 2014/0230021 A1 Aug. 14, 2014

Related U.S. Application Data

(62) Division of application No. 13/267,315, filed on Oct. 6, 2011, now Pat. No. 8,707,392.

(Continued)

(51) Int. Cl.
*H04B 7/00* (2006.01)
*H04W 12/08* (2009.01)
(Continued)

(52) U.S. Cl.
CPC ............ *H04W 12/08* (2013.01); *G06F 19/323* (2013.01); *G06F 19/3481* (2013.01); *H04W 12/06* (2013.01); *H04W 12/04* (2013.01)

(58) Field of Classification Search
CPC ... G06F 19/323; G06F 19/3481; H04W 12/06; H04W 12/08
(Continued)

(56) References Cited

U.S. PATENT DOCUMENTS 8,588,687 B2 * 11/2013 Ramey ............... A61B 5/14532
455/41.2
2004/0073464 A1 * 4/2004 Huang ................. A61B 5/0002
705/3

(Continued)

OTHER PUBLICATIONS

Part 20601: Application Profile—Optimized Exchange Protocol, IEEE Std 11073-20601, Sep. 26, 2008.

(Continued)

*Primary Examiner* — Ayodeji Ayotunde
(74) *Attorney, Agent, or Firm* — Harness, Dickey

(57) ABSTRACT

A computer-implemented diabetes management system is provided that supports enhanced security between a diabetes care manager in data communication with a medical device. The diabetes care manager includes: a first application that operates to request access to a first security role supported by the medical device, where the first security role is associated with a first set of commands for accessing data on the medical device that are defined as a private extension of the communication protocol; and a second application that operates to request access to a second security role supported by the medical device, where the second security role is associated with a second set of commands for accessing data on the medical device that are defined as a private extension of the communication protocol. The second set of commands has one or more commands that are mutually exclusive from the first set of commands.

16 Claims, 21 Drawing Sheets

Related U.S. Application Data

(60) Provisional application No. 61/393,567, filed on Oct. 15, 2010.

(51) Int. Cl.
   *G06F 19/00* (2011.01)
   *H04W 12/06* (2009.01)
   *H04W 12/04* (2009.01)

(58) Field of Classification Search
   USPC .......................................... 455/500, 507, 509
   See application file for complete search history.

(56) References Cited

U.S. PATENT DOCUMENTS

2009/0006061 A1* 1/2009 Thukral ................ G06F 19/325
   703/11
2009/0006133 A1* 1/2009 Weinert ............. A61B 5/14532
   705/3

OTHER PUBLICATIONS

Part 10417: Device Specialization—Glucose Meter, IEEE Std 11073-10417, May 8, 2009.
Continua Design Guidelines 2010, Oct. 1, 2010.
Skevofilakas et al., A Communication and Information Technology Infrastructure for Real Time Monitoring and Management of Type 1 Diabetes Patients, IEEE, Aug. 2007.
Mougiakakou et al., A Communication Platform for Tele-monitoring and Tele-management of Type 1 Diabetes, IEEE, Sep. 2005.
Mougiakakou et al. SMARTDIAB: A Communication and Information Technology Approach for the Intelligent Monitoring, Management and Follow-up of Type 1 Diabetes Patients, IEEE, May 2010.

* cited by examiner

COEXISTENCE OF MULTIPLE RADIOS IN A MEDICAL DEVICE

CROSS-REFERENCE TO RELATED APPLICATION

This application is a divisional of U.S. Ser. No. 13/267,315 filed Oct. 6, 2011 which claims the benefit of U.S. Provisional Application No. 61/393,567, filed on Oct. 15, 2010. The entire disclosures of the above applications are incorporated herein by reference.

FIELD

The present disclosure relates to disease management device systems and methods that support arbitrating priority among multiple communication modules.

BACKGROUND

Daily diagnostic information, such blood glucose, is typically obtained from a capillary blood sample with a lancing device and is then measured with a handheld blood glucose meter (hereinafter handheld device). To effectively manage the care and health of the patient, there is a need for the handheld device to communicate with other medical devices and systems. The other medical devices and systems, however, may use different communication protocols and interfaces (e.g., Bluetooth protocol, universal serial bus (USB) interface, etc.). Accordingly, there is a need for the handheld device to include multiple communication protocols and interfaces that enable the handheld device to communicate with the other medical devices and systems in a safe and secure manner.

Additionally, in order to communicate securely and reliably, the handheld device may need to establish a secure communication link between itself and the other medical devices and systems. Such a process may require a user (such as a patient with reduced visual acuity and/or technical skill) to follow a complex procedure that requires extensive user input. Additionally, in order for those other medical devices and systems to communicate between themselves securely and reliably, each device/system may need to establish a secure communication link between itself and the other medical devices and systems. To establish each such communication link, a user (such as a patient with reduced visual acuity and/or technical skill) may have to perform a complex procedure that requires extensive user input, which is inefficient subject to error. Accordingly, there is a need for a method of establishing a secure communication link between a handheld device and other medical devices/systems that is relatively simple and reduces the number and complexity of user inputs.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer-implemented diabetes management system is provided that supports enhanced security between a diabetes care manager in data communication with a medical device. The diabetes care manager includes: a first application that operates to request access to a first security role supported by the medical device, where the first security role is associated with a first set of commands for accessing data on the medical device that are defined as a private extension of the communication protocol; and a second application that operates to request access to a second security role supported by the medical device, where the second security role is associated with a second set of commands for accessing data on the medical device that are defined as a private extension of the communication protocol. The second set of commands has one or more commands that are mutually exclusive from the first set of commands.

In another aspect of this disclosure, the diabetes care manager further includes: a meter that measures the concentration of glucose in blood; a collection application that executes a structured collection procedure for obtaining measurement data from the meter and provides access to the measurement data, where the structured collection procedure having parameters including a schedule of collection events; a configuration application that accesses and manipulates the parameters of the structured collection procedure using a set of action commands, where the set of action commands are defined in compliance with the communication protocol; and a collection interface that receives an action command from the configuration application, executes the received action command and issues a response command in response thereto, wherein the response command is defined in compliance with the communication protocol.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals may indicate corresponding parts throughout the several views of the drawings.

DETAILED DESCRIPTION

Figure 1:
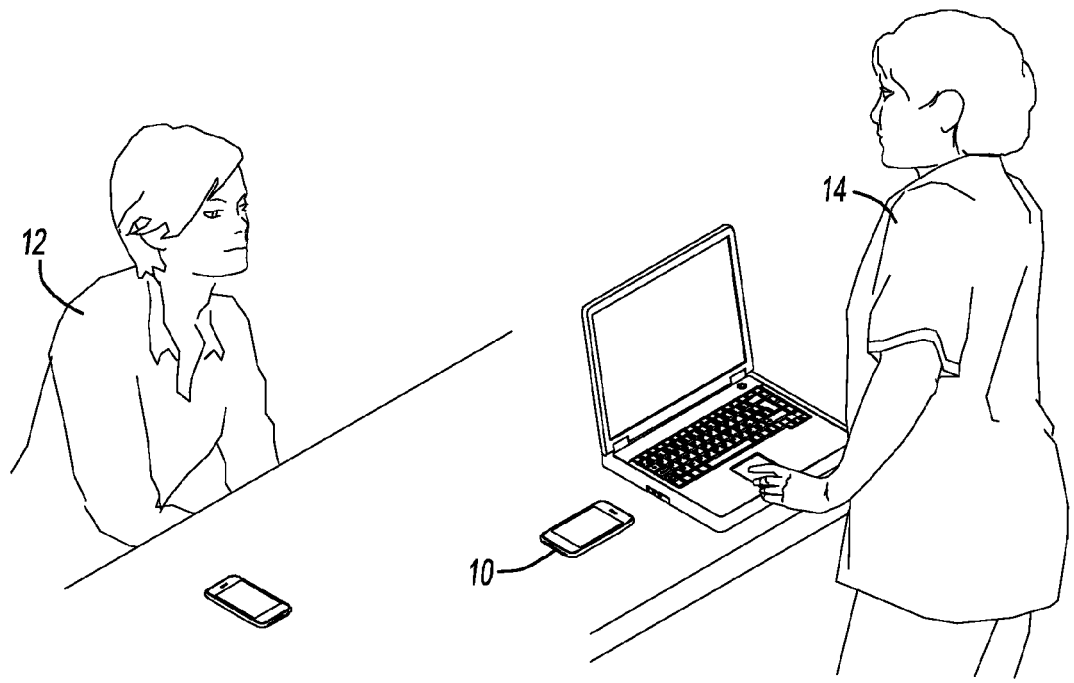
FIG. 1 shows a patient and a treating clinician with a handheld diabetes manager according to the present teachings.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

As used herein, the term "module" can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term "module" can include memory (shared, dedicated, or group) that stores code executed by the processor.

The term "code," as used above, can include software, firmware, and/or microcode, and can refer to programs, routines, functions, classes, and/or objects. The term "shared," as used above, means that some or all code from multiple modules can be executed using a single (shared) processor. In addition, some or all code from multiple modules can be stored by a single (shared) memory. The term "group," as used above, means that some or all code from a single module can be executed using a group of processors. In addition, some or all code from a single module can be stored using a group of memories.

The apparatuses and methods described herein can be implemented by one or more computer programs executed by one or more processors. The computer programs include processor-executable instructions that are stored on a non-transitory, tangible, computer readable medium. The computer programs can also include stored data. Examples of the non-transitory, tangible, computer readable medium include, but are not limited to, nonvolatile memory, magnetic storage, and optical storage.

Example embodiments will now be described more fully with reference to the accompanying drawings.

Handheld Diabetes Management Device with Touchscreen Display

Figure 2:
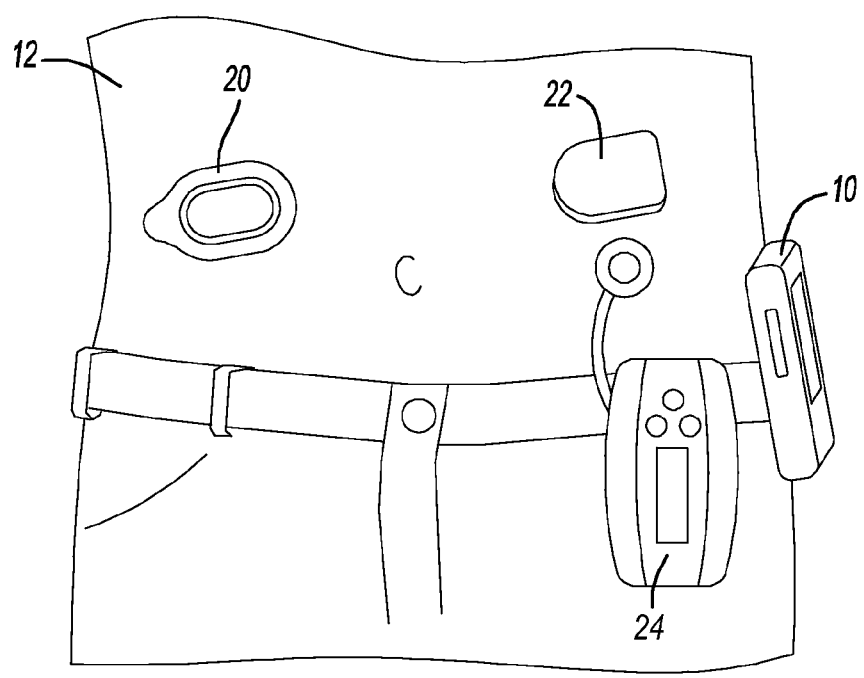
FIG. 2 shows a patient with an exemplary continuous glucose monitor (CGM), first ambulatory insulin infusion pump, second ambulatory insulin infusion pump, and handheld diabetes manager.

With initial reference to FIG. 1, a handheld diabetes manager constructed in accordance to one example of the present teachings is shown and generally identified at reference numeral 10. FIG. 1 also shows a patient 12 with diabetes and a clinician 14 in a clinic environment, the clinician 14 and patient 12 discussing various devices for managing diabetes including the handheld diabetes manager 10. For illustrative purposes, FIG. 2 shows the patient 12 with diabetes with the handheld diabetes manager 10, a continuous glucose monitor (CGM) 20, a first ambulatory insulin infusion pump 22, and a second ambulatory insulin infusion pump 24.

Persons with diabetes include persons with metabolic syndrome, pre-diabetes, type 1 diabetes, type 2 diabetes, gestational diabetes, and other types of diabetes and are collectively referred to as the patient 12 herein. Healthcare providers for diabetes are diverse and include nurses, nurse practitioners, physicians, and endocrinologists and are collectively referred to as the clinician 14 herein. During a healthcare consultation, a patient 12 typically shares with a clinician 14 a variety of patient data including blood glucose measurements, continuous glucose monitor data, insulin infused, food and beverages consumption, exercise, and other lifestyle information. This patient data can be recorded manually on a patient diary or other tools such as an Accu-Chek® 360 View Blood Glucose Analysis System form or electronically on a handheld diabetes manager, such as the handheld diabetes manager 10, or electronically on personal computer using diabetes analysis software, or electronically on a web-based diabetes analysis site, or a combination of these means. The clinician 14 will often obtain additional patient biomarker data such as measurements of HbA1C, cholesterol levels, triglycerides, blood pressure, and weight. The clinician 14 can analyze the patient data using manual techniques, electronically using diabetes analysis software, or a web-based diabetes analysis site, or a combination of these means. After analyzing the patient data along with the patient's adherence to the previously prescribed therapy, the clinician 14 can decide whether to modify the therapy for the patient 12. In considering whether to modify the therapy, the clinician 14 may need to balance the interests of the patient 12, the payer (not shown), and the clinician 14.

Figure 3:
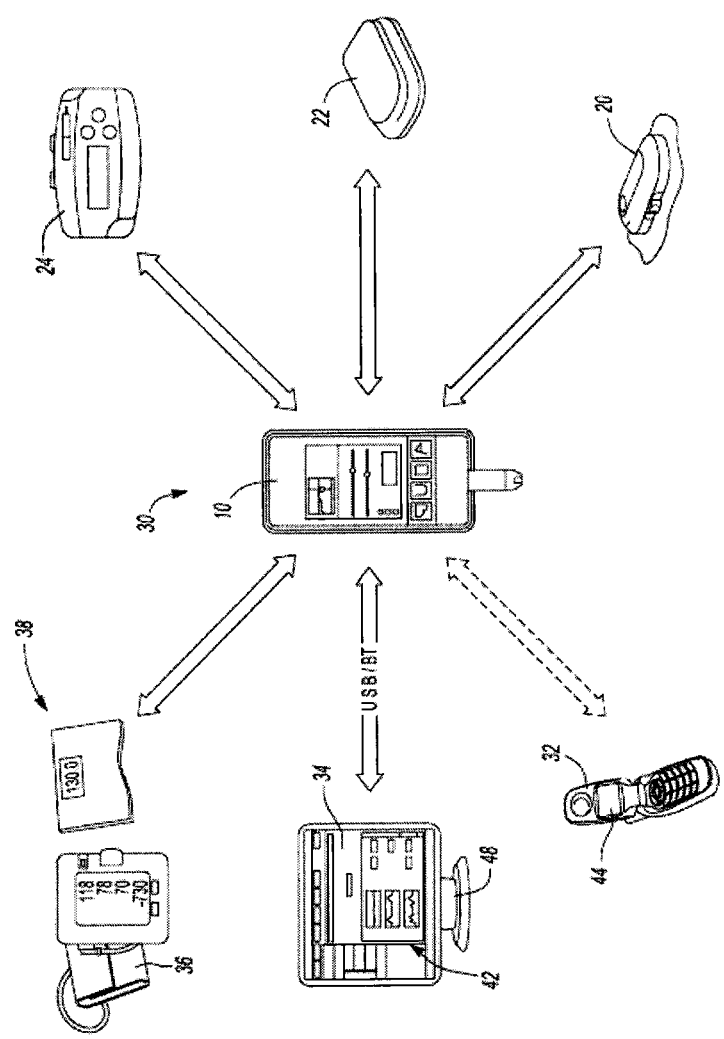
FIG. 3 shows an exemplary diabetes care system of devices used by patients and clinicians to manage diabetes.
Figure 4:
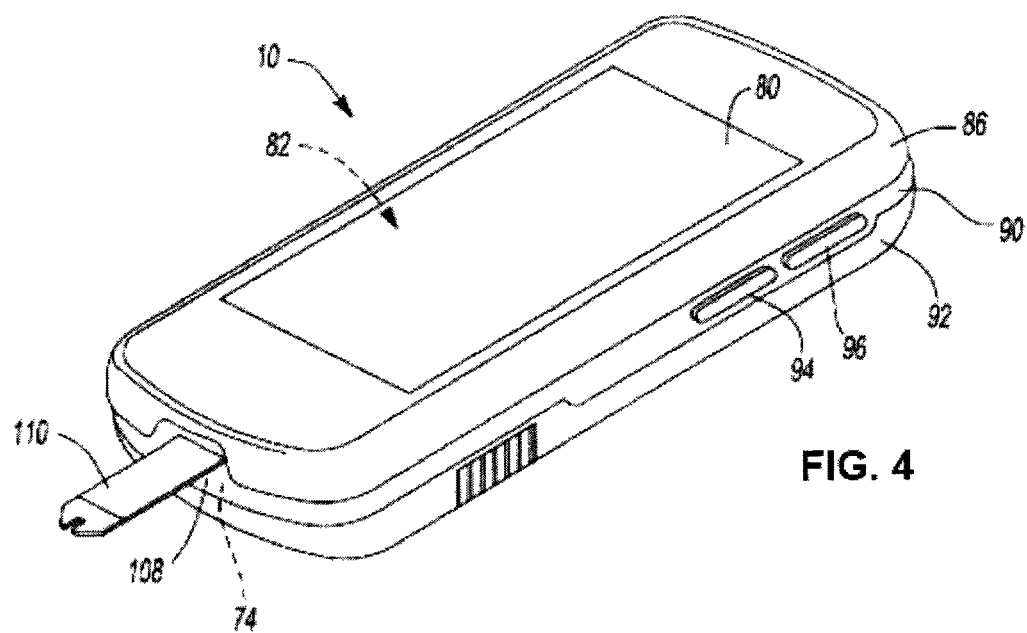
FIGS. 4-8 show various isometric views of the handheld diabetes manager of FIG. 1.
Figure 5:
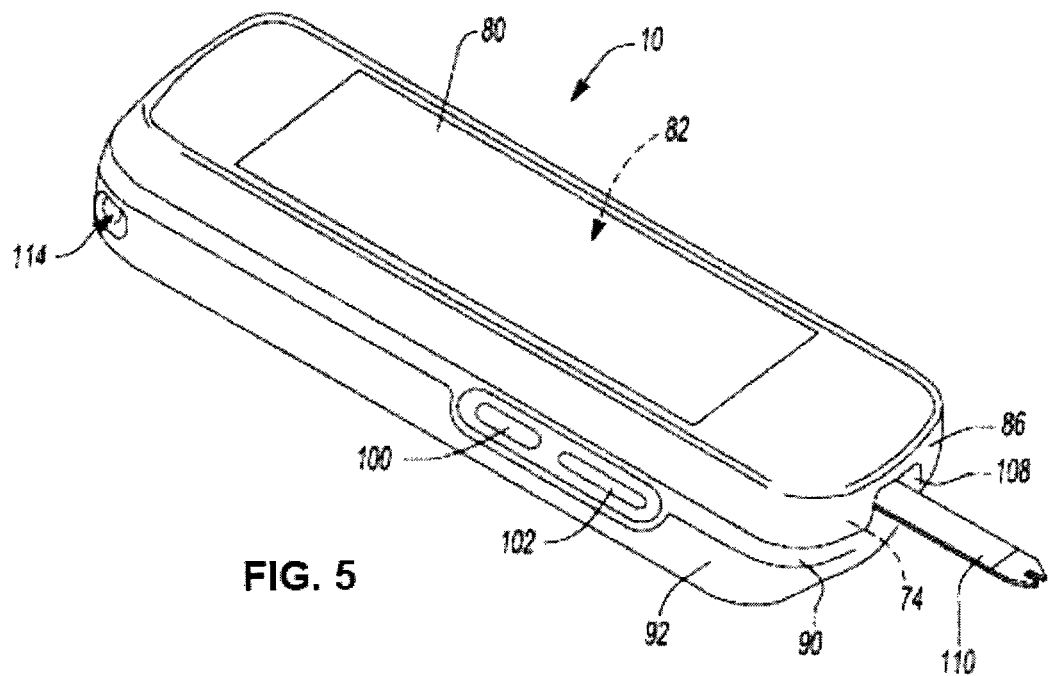
Figure 6:
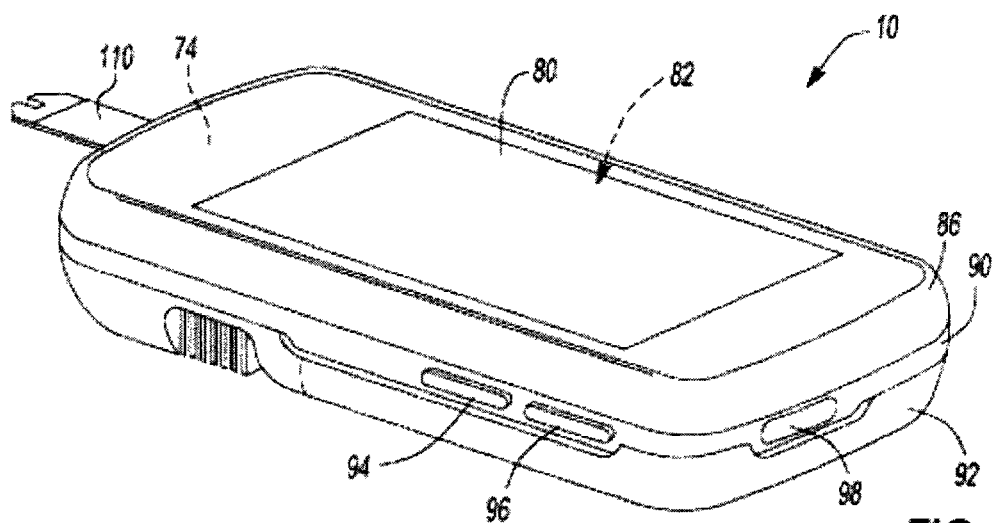
Figure 7:
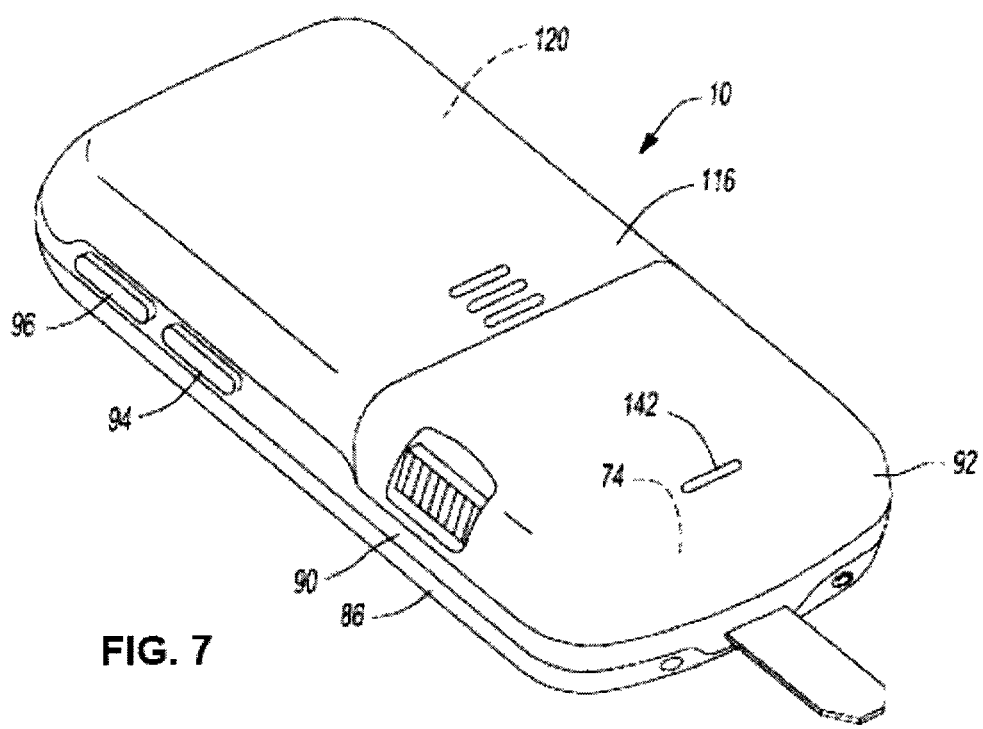
Figure 8:
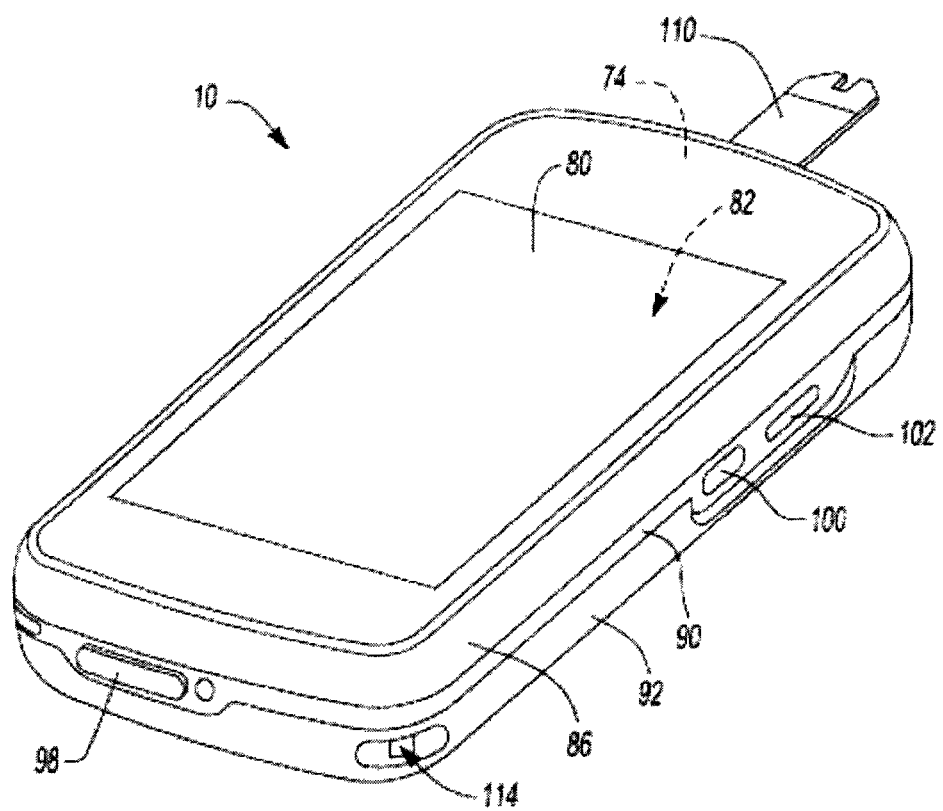

FIG. 3 shows a diabetes care system of devices 30 used by clinicians and patients with diabetes to manage diabetes according to the present teachings. The system of devices 30 can include one or more of the following devices: the handheld diabetes manager 10, the first ambulatory insulin infusion pump 22, the second ambulatory insulin infusion pump 24, the continuous glucose monitor (CGM) 20, the mobile phone 32, diabetes analysis software and pump configuration software 34, a health (such as blood pressure) monitor 36 and various health care devices 38. The handheld diabetes manager 10 is configured as the system hub in this embodiment. However, other devices such as the first ambulatory insulin infusion pump 22 or the mobile phone 32 can serve as the system hub according to other embodiments. Communications among the system of devices 30 can be performed using, for example, a wireless protocol such as Bluetooth or a proprietary protocol that operates IEEE 11073 as extended using guidelines provided by the Continual® Health Alliance Design Guidelines. Healthcare records systems such as Microsoft® HealthVault™ and Google™ Health can be used by the patient 12 and clinician 14 to exchange information. The CGM 20 uses a subcutaneous sensor to sense and monitor the amount of glucose in the blood of the patient 12 and communicates corresponding readings to the handheld diabetes manager 10.

The handheld diabetes manager 10 performs various tasks including measuring and recording blood glucose levels, determining an amount of insulin to be administered to the patient 12 via the insulin infusion pump 22 or 24, receiving patient data via a user interface, archiving the patient data, etc. The handheld diabetes manager 10 periodically receives readings from the CGM 20 indicating insulin level in the blood of the patient 12. The handheld diabetes manager 10 transmits instructions to the insulin infusion pump 22 or 24, which delivers insulin to the patient 12. Insulin can be delivered in a scheduled manner in the form of a basal dose, to maintain a predetermined insulin level in the blood of the patient 12. Additionally, insulin can be delivered in the form of a bolus dose, which raises the amount of insulin in the blood of the patient 12 by a predetermined amount.

The CGM patch 20 is a user-wearable continuous glucose monitoring patch. The CGM patch 20 collects CGM data and wirelessly transmits the CGM data to the handheld diabetes manager 10.

The mobile messenger 44 can be a mobile phone, pager, or other communications system. The mobile messenger 44 comprises a messenger subsystem that formats messages selected for transmission to an external communications network (not shown). The mobile messenger 44 accepts message requests from the handheld diabetes manager 10.

The health care devices 38 can include the health monitor 36, weight scale, pedometer, fingertip pulse oximeter, thermometer, or other device that obtains personal health information and is capable of communicating the health information to the handheld diabetes manager 10 through a data output channel such as a wireless or USB transport using a communications protocol such as ISO/IEEE 11073 extended using guidelines from Continual® Health Alliance.

The first insulin infusion pump 22 can have an insulin reservoir and can be configured to deliver insulin to the patient 12. The first insulin infusion pump 22 can also communicate data to the handheld diabetes manager 10. The data can include amounts of insulin delivered to the patient 12, corresponding times of delivery, and pump status. The handheld diabetes manager 10 and the first insulin infusion pump 22 can communicate using a wireless communication protocol such as Bluetooth. Other wireless or wireline communication protocols can also be used. It will be appreciated that the second insulin infusion pump 24 can be configured similarly.

The handheld diabetes manager 10 includes a blood glucose measurement engine 74. The blood glucose measurement engine 74 can determine a blood glucose value derived from a blood sample placed on a test strip as will be described herein.

With general reference now to FIGS. 4-8, additional features of the handheld diabetes manager 10 will be described. The handheld diabetes manager 10 is designed to have an appearance similar to a consumer electronics device and a popular Windows CE operating system, so persons with diabetes can manage their diabetes more discretely using a more familiar user interface. The handheld diabetes manager 10 can have a touch screen 80 that supports gesturing. The touch screen 80 overlays a thin film transistor (TFT) display 82. The TFT display 82 can display multiple colors for graphic displays for an improved user interface and the presentation of video. In one example, the TFT display 82 can be a liquid crystal diode (TFT-CD) display. The touch screen 80 can be a resistive touch screen. A top housing 86 can generally support the touch screen 80 at a position intermediate the touch screen 80 and the TFT display 82.

A center frame 90 can be positioned generally between the top housing 86 and a bottom housing 92. The center frame 90 can generally support buttons 94 and 96 on one side (FIG. 4) and provide access to a USB port 100 and SD port 102 on an opposite side. The buttons 94 and 96 can be indexing buttons. The center frame 90 can also define an access port 108 for insertion of a test strip 110 to perform blood glucose measurements using the blood glucose measurement engine 74. The bottom housing 92 can further comprise a lanyard 114. The lanyard 114 can be used to support a flexible member, such as a string or lace for attaching to the handheld diabetes manager 10. A battery cover 116 can be slidably coupled to the bottom housing 92 to securely retain a battery (not shown) relative to the bottom housing 92. The battery can be a user-replaceable single lithium-ion battery with integrated safety circuit.

Figure 9:
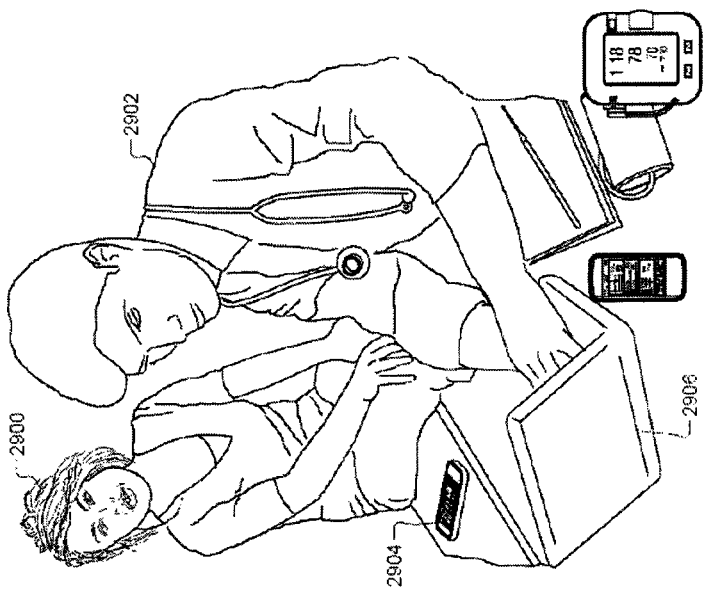
FIG. 9 shows a patient and a health care professional along with various devices that can be used to help the patient monitor and control health.

Referring to FIG. 9, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Figure 10:
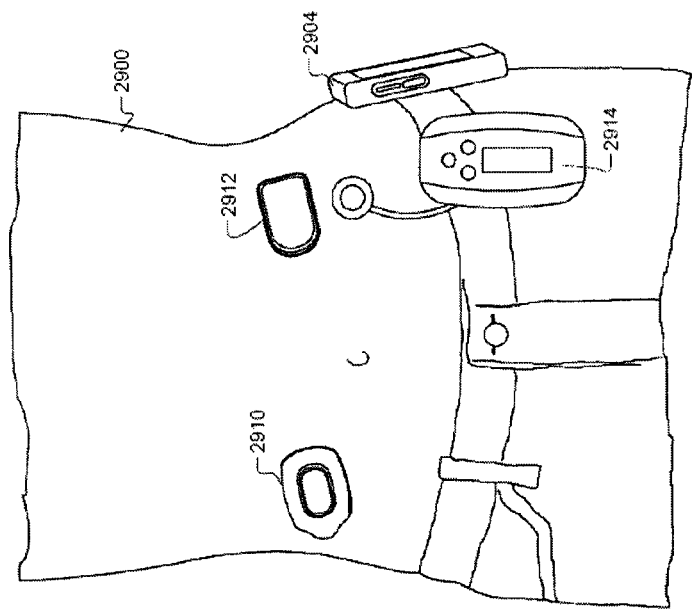
FIG. 10 shows a patient with a continuous glucose monitor (CGM), an ambulatory durable insulin infusion pump, an ambulatory non-durable insulin infusion pump, and a blood glucose (bG) management device.

Referring to FIG. 10, the patient 2900 can use a continuous glucose monitor (CGM) 2910, an ambulatory non-durable insulin infusion pump 2912 or an ambulatory durable insulin infusion pump 2914 (hereinafter insulin pump 2912 or 2914), and the handheld diabetes management device 2904 (hereinafter the diabetes manager 2904). The CGM 2910 uses a subcutaneous sensor to sense and monitor the amount of glucose in the blood of the patient 2900 and communicates corresponding readings to the diabetes manager 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives readings from the CGM 2910 indicating insulin level in the blood of the patient 2900. The diabetes manager 2904 transmits instructions to the insulin pump 2912 or 2914, which delivers insulin to the patient 2900. Insulin can be delivered in a scheduled manner in the form of a basal dose, which maintains a predetermined insulin level in the blood of the patient 2900. Additionally, insulin can be delivered in the form of a bolus dose, which raises the amount of insulin in the blood of the patient 2900 by a predetermined amount.

Figure 11:
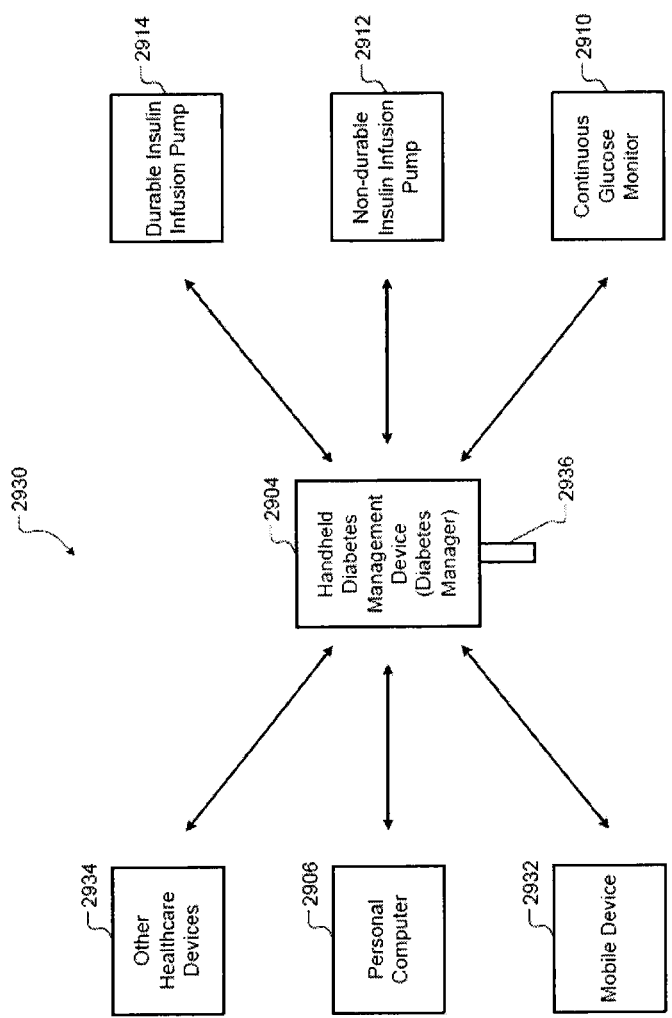
FIG. 11 shows a diabetes care system of systems that can be used to manage diabetes.

Referring to FIG. 11, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the PC 2906 with the diabetes analysis software, and other healthcare devices 2934. The diabetes manager 2904 is configured as a system hub and communicates with the devices of the diabetes management system 2930. Alternatively, the insulin pump 2914 or the mobile device 2932 can serve as the system hub. Communication between the devices in the diabetes management system 2930 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive blood glucose readings from one or more sources (e.g., from the CGM 2910). The CGM 2910 continuously measures the blood glucose level of the patient 2900. The CGM 2910 periodically communicates the blood glucose level to the diabetes manager 2904. The diabetes manager 2904 and the CGM 2910 communicate wirelessly using a proprietary Gazell wireless protocol developed by Nordic Semiconductor, Inc.

Additionally, the diabetes manager 2904 includes a blood glucose meter (BGM) and a port that communicates with the BGM (not shown). The port can receive a blood glucose measurement strip 2936. The patient 2900 deposits a sample of blood or other bodily fluid on the blood glucose measurement strip 2936. The BGM analyzes the sample and measures the blood glucose level in the sample. The blood glucose level measured from the sample and/or the blood glucose level read by the CGM 2910 can be used to determine the amount of insulin to be administered to the patient 2900. To facilitate collection of blood glucose measures, the diabetes manager 2904 may executes one or more structured collection procedures as further described below.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with the other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 may use communication protocols compliant with ISO/IEEE 11073. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a pager, or a personal digital assistant (PDA). The diabetes manager 2904 can send messages to an external network through the mobile device 2932. The mobile device 2932 can transmit messages to the external network upon receiving requests from the diabetes manager 2904.

Figure 12:
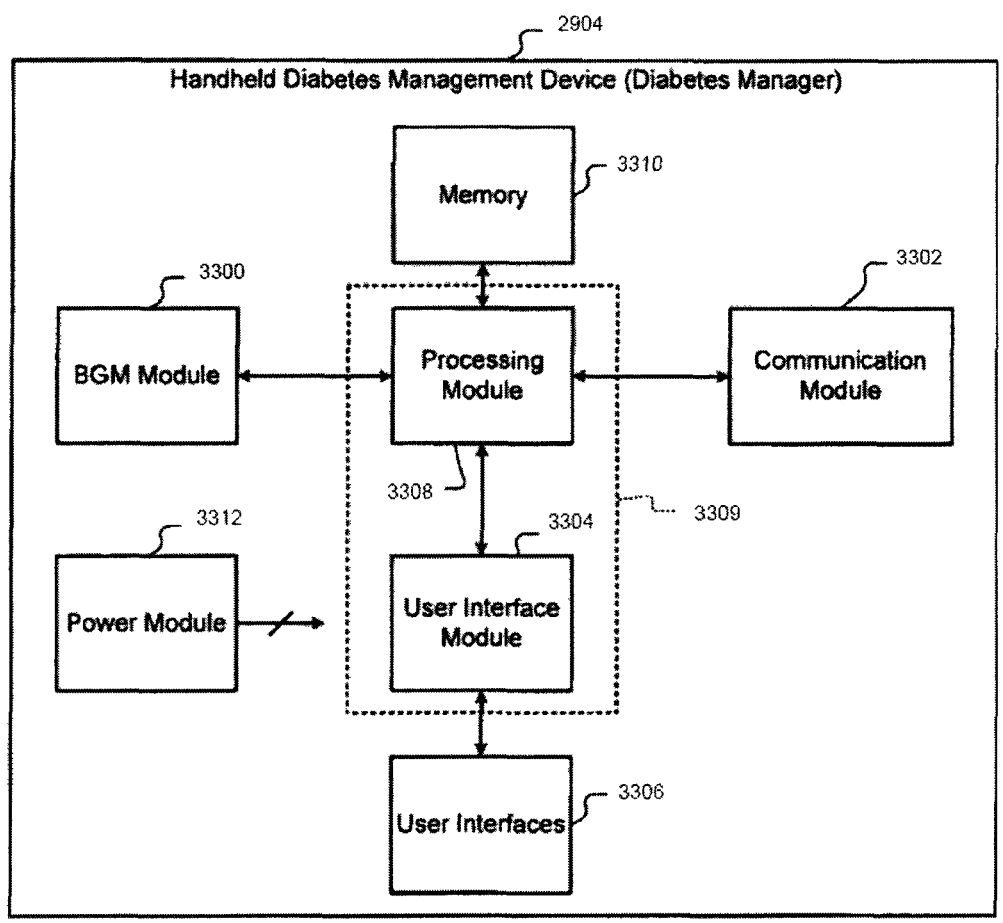
FIG. 12 is a functional block diagram of a diabetes manager.

An exemplary diabetes manager 2904 is further described in relation to FIG. 12. The diabetes manager 2904 comprises a blood glucose measuring (BGM) module 3300, a communication module 3302, a user interface module 3304, user interfaces 3306, a processing module 3308, memory 3310, and a power module 3312. The user interface module 3304 and the processing module 3308 can be implemented by an application processing module 3309. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices of the diabetes management system 2930. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The processing module 3308 outputs data to and receives data from the user interfaces 3306 via the user interface module 3304. The processing module 3308 outputs data to and receives data from the devices of the diabetes management system 2930 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

For purposes of this disclosure, the diabetes manager 2904 serves as a collection device. However, the collection device can be any portable electronic device that can provide an acquisition mechanism for determining and storing physiological measures of a person. For example, self-monitoring blood glucose meters and continuous glucose monitor devices are examples of collection devices used in diabetes care. While this disclosure makes reference to diabetes care, it is readily understood that the concepts disclosed herein can be applied to other types of chronic diseases and/or collection devices.

Figure 13:
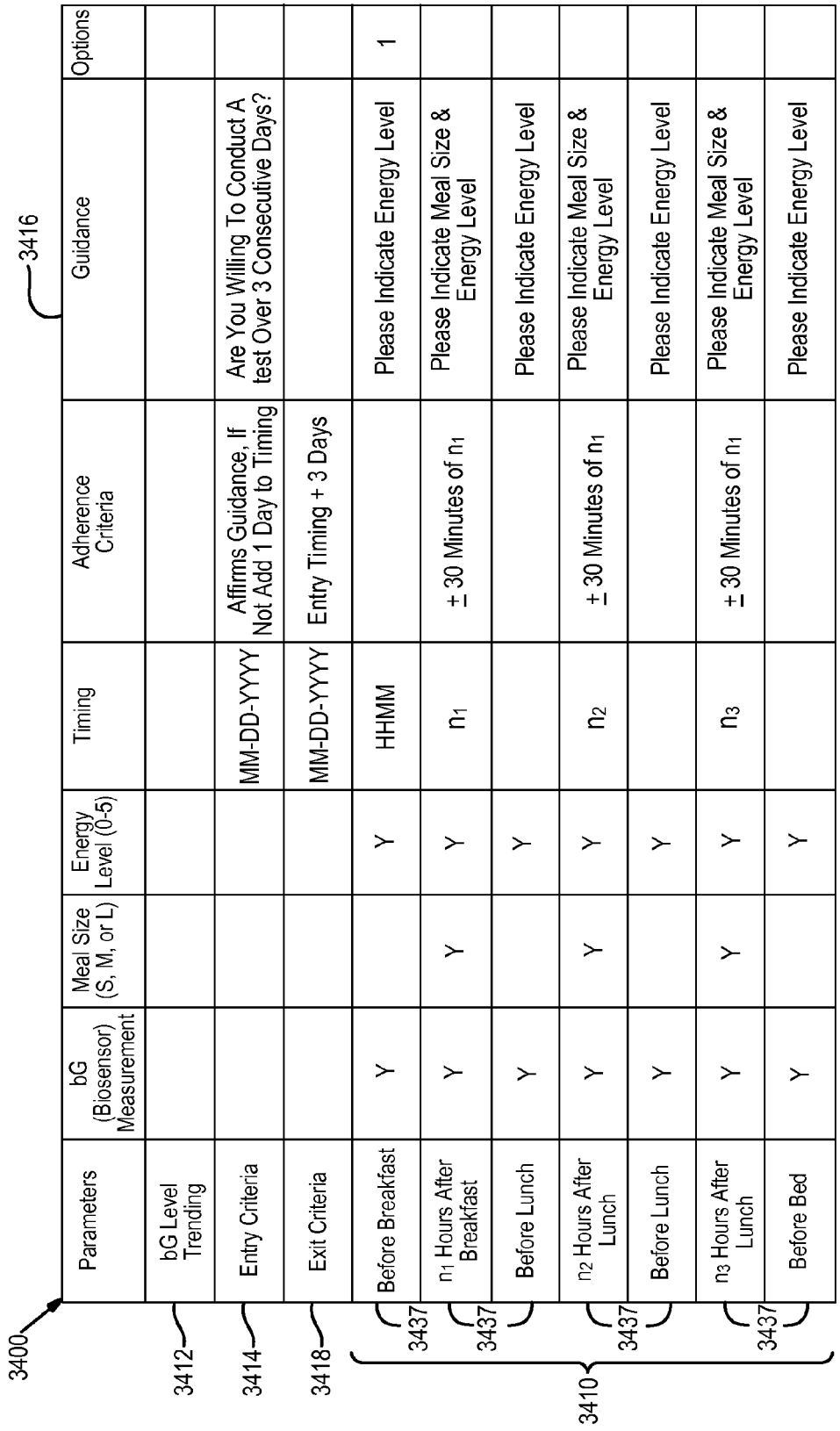
FIG. 13 is a chart that conceptually illustrates an exemplary structured collection procedure.

In the diabetes care domain, a structured test or structure collection procedure is a particular type of treatment plan. FIG. 13 conceptually illustrates an exemplary structured collection procedure 3400 comprised of a plurality of parameters that define the procedure. A structured collection procedure is primarily comprised of a series of planned actions or collection events 3410 for obtaining measurement data using the collection device. Each collection event is a request for a physiological measure obtained using the collection device or other input by the patient into the collection device. In the illustrated procedure, the requests are for a bG measurement. A given collection event may require additional input such as an indication of meal size or an indication of the patient's energy level.

In addition to a series of collection events, the structured collection procedure 3400 may include other types of parameters such as a medical use case 3412, an entry criterion 3414, an adherence criterion 3416 and an exit criterion 3418. Medical use case 3412 provides an indication of when the particular procedure may be applicable. In this case, the collection procedure is helpful for determining trends in blood glucose (bG) levels of a patient and/or relationships between blood glucose and other parameters, such as time of day, meal size, energy level, etc. Entry criterion 3414 establishes the conditions needed to be met prior to obtaining a physiological measure from the patient. Adherence criterion 3416 is used to assess qualitatively whether a given collection event was performed. Exit criterion 3418 establishes the conditions needed to be met prior to exiting the structured collection procedure. It is readily understood that other types of parameters may be used to define a structured collection procedure. Further information regarding structure collection procedures may be found in US Patent Application Publication No. 2010/0212675 entitled "Structured Testing Method for Diagnostic or Therapy Support of a Patient with a Chronic Disease and Devices Thereof" which is incorporated by reference herein.

Figure 15:
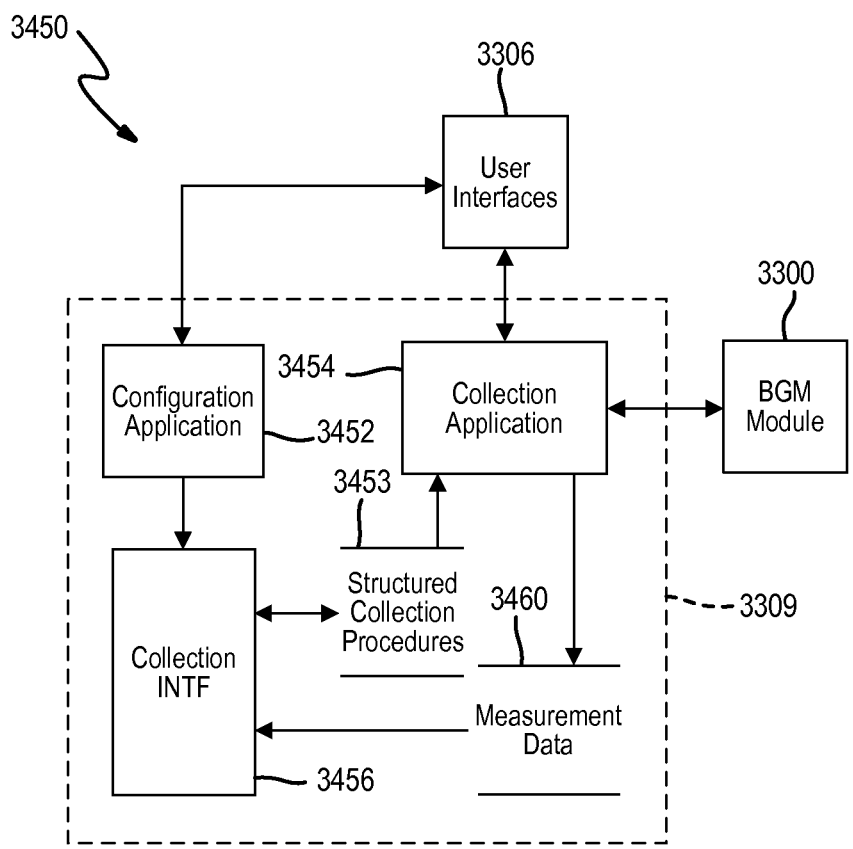
FIG. 15 is a diagram depicting an exemplary system that supports remote configuration of such structure collection procedures.

Structured collection procedures are typically implemented on a collection device, such as diabetes manager 2904. FIG. 15 depicts an exemplary system 3450 that supports remote configuration of such structure collection procedures by a configuration application 3452. In an exemplary embodiment, the application processing module 3309 of the diabetes manager 2904 is further defined to support configuration. The application processing module 3309 include a configuration application 3452, a collection application 3454 and a collection interface 3456; each of these components may be implemented as computer executable instructions in a data store of the collection device. One or more structured collection procedures may also reside in a data store 3458 accessible to the collection application 3454.

During operation, the collection application 3454 executes a structured collection procedure to obtain measurement data from the patient. In a simplified example, the collection application 3454 may interact with a user interface 3306 to prompt a patient to take a glucose measure. The patient may be prompted at a particular time of day as specified by the structured collection procedure. The collection application 3454 is interfaced with the BGM module 3300 to receive blood glucose measures obtained from the patient and store such measures in a data store residing on the collection device. The collection application 3454 may also interact with the user interface 3306 to obtain other input from the patient in accordance with the structured collection procedure.

The collection interface 3456 in turn provides access to the blood glucose measures and other related measurement data. In the exemplary embodiment, measurement data is accessed via the collection interface 3456 using a communication protocol defined in accordance with IEEE standard 11073-20601. In the case of blood glucose measures, the collection interface 3456 may implement a device specialized communication protocol as defined by IEEE standard 11073-10417. For other types of measures, it is understood that the collection interface 3456 may implement the applicable specialized communication protocol.

Over time, the parameters associated with a structured collection procedure residing on the collection device may need to be configured or otherwise modified by a tending healthcare provider. The configuration application 3452 provides the mechanism by which the parameters of a structured collection procedure may be accessed and manipulated by the healthcare provider. For example, the configuration application 3452, interacting with suitable user interfaces, enables the healthcare provider to select a structured collection procedure associated with a given patient. Parameters associated with the select collection procedure are then displayed to the healthcare provider. The healthcare provider may modify and save one or more of the parameters associated with the selected collection procedure. In one exemplary embodiment, the configuration application 3452 may reside on the collection device. In this embodiment, the configuration application 3452 interacts with the user interfaces 3306 residing on the collection device as shown in FIG. 15.

Figure 16:
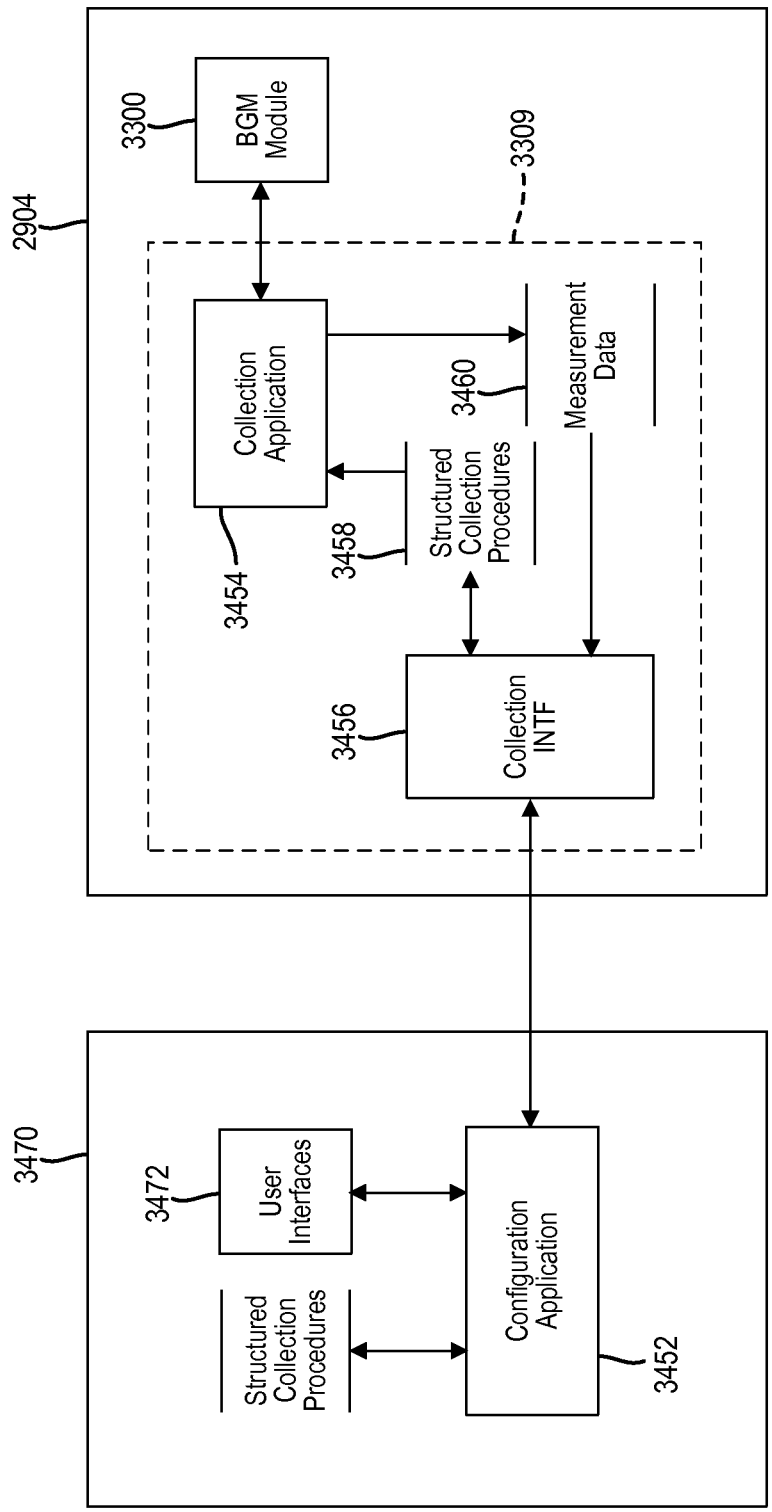
FIG. 16 is a diagram depicting another exemplary system that supports remote configuration of such structure collection procedures.

In another exemplary embodiment, the configuration application 3452 may reside on a device 3470 distinct and remote from the collection device as shown in FIG. 16. For example, the device 3470 may be a personal computer that resides with the healthcare provider. In this embodiment, the configuration application 3452 interacts with user interfaces 3472 residing on the device 3470 to access and manipulate the structured collection procedure, where the structured collection procedures are stored in a data store on the device 3470. Once healthcare provider has updated a given structure collection procedure locally, the configuration application 3452 will then interact with the collection interface to update the corresponding structured collection procedure on the collection device.

To do so, the configuration application 3452 interfaces with the collection interface 3456 using a set of action commands to update parameters of a structured collection procedure residing at the collection device. Of note, the set of action commands are defined in compliance with the communication protocol used to access the measurement data. In the exemplary embodiment, the collection interface 3456 accesses the blood glucose measures using the IEEE standard 11073-10417. Thus, the set of action commands used to access and manipulate the parameters of a structured collection procedure are defined as a private extension of the IEEE standard 11073-10417 as will be further described below.

ISO/IEEE 11073 standard enables communication amongst medical devices and other computer systems. By way of background, ISO/IEEE 11073 standard is based on an object oriented systems management paradigm. The overall system model is divided into three principal components: the domain information model (DIM), the service model, and the communication model. These three components work together to represent data, define data access and command methodologies and communicate the data from an agent to a manager. ISO/IEEE 11073-20601 may be referenced for a detailed description of the modeling constructs although each is described briefly below.

Figure 17:
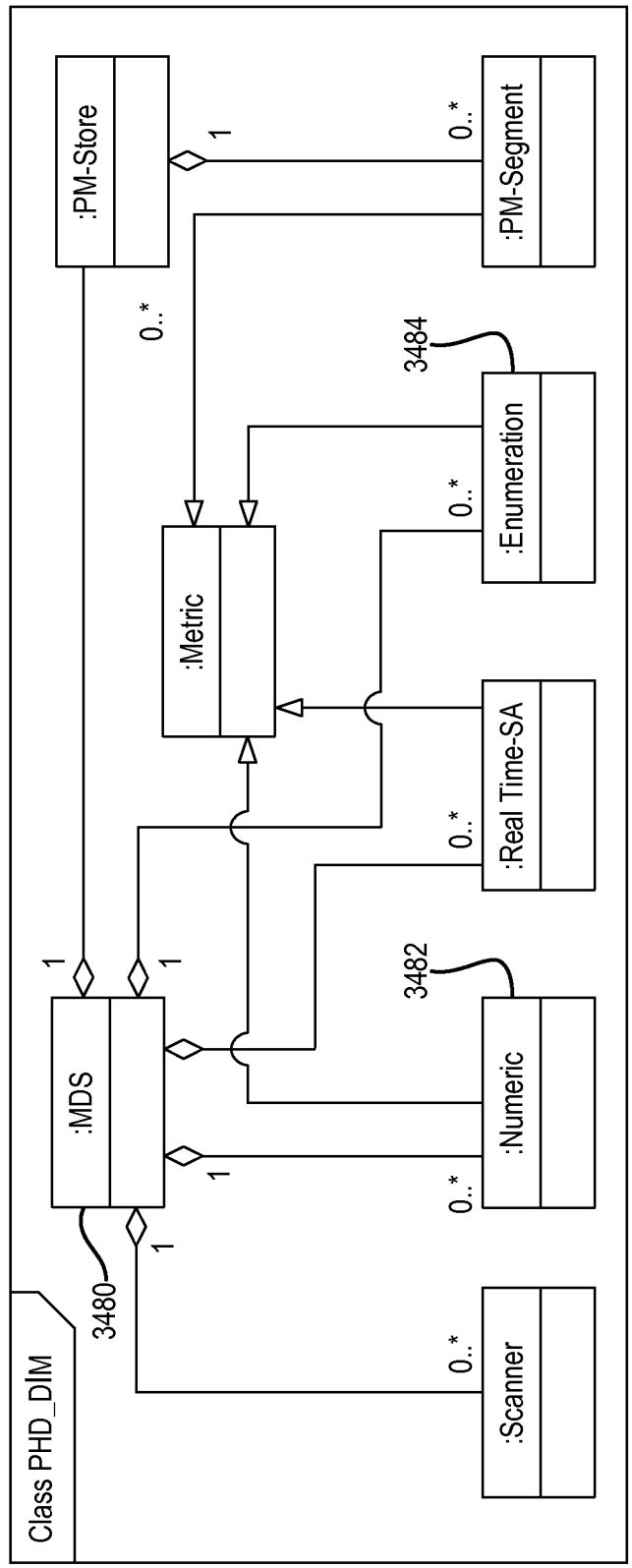
FIG. 17 is a class diagram for a personal health device defined in accordance with ISO/IEEE 11073-20601.

The domain information model is a hierarchical model that describes an agent as a set of objects. These objects and their attributes represent the elements that control behavior and report on the status of the agent and the data that an agent can communicate to a manager. With reference to FIG. 17, a class diagram for a personal health device is defined in accordance with ISO/IEEE 11073-20601. The Medical Device System class 3480 is the root class of the device and contains attributes defining the device itself. Exemplary attributes include the type of device, i.e., glucose meter or insulin pump, manufacturer and model information and registered certification information. All other object classes are derived from the MDS class. For example, the Numeric class represents numeric measurements such as bG, carbohydrates, bolus amount, etc; whereas, the enumeration class represents status information and/or annotation information. For brevity purposes, a description is not provided for all of the classes shown in the figure.

Communication between the agent and the manager is defined by the application protocol in ISO/IEEE 11073-20601. The service model defines the conceptual mechanisms for the data exchange services. Object access services, such as Get, Set, Action and Event Reports, are mapped to messages that are exchanged between the agent and the manager. Protocol messages within the ISO/IEEE 11072 series of standards are defined in ASN.1. The messages defined in ISO/IEEE 11073-20601 can coexist with messages defined in other standard application profiles defined in the ISO/IEEE 11072 series of standards.

In general, the communication model supports the topology of one or more agents communicating over logical point-to-point connections to a single manager. More specifically, the communication model defines the construct of an application protocol data unit (APDU). ADPUs are data packets exchanged between agents and managers. For each logical point-to-point connection, the dynamic system behavior is defined by a connection state machine as specified in ISO/IEEE 11073-20601.

Two styles of configuration are defined in ISO/IEEE 11073-20601: standard and extended. Standard configurations are defined in the ISO/IEEE 11073-104zz specializations (such as the ISO/IEEE 11073-10417 Glucose Device specialization) and are assigned a well-known identifier (Dev-Configuration-Id). The usage of a standard configuration is negotiated at association time between the agent and the manager. If the manager acknowledges that it understands and wants to operate using the configuration, then the agent can begin sending measurements immediately. If the manager does not understand the configuration, the agent provides the configuration prior to transmitting measurement information.

In extended configurations, the agent's configuration is not predefined in a standard. The agent determines which objects, attributes, and values will be used in a configuration and assigns a configuration identifier. When the agent associates with a manager, it negotiates an acceptable configuration. Typically, the manager does not recognize the agent's configuration on the first connection, so the manager responds that the agent needs to send the configuration information as a configuration event report. If, however, the manager already understands the configuration, either because it was preloaded in some way or the agent had previously associated with the manager, then the manager responds that the configuration is known and no further configuration information needs to be sent.

Figure 14:
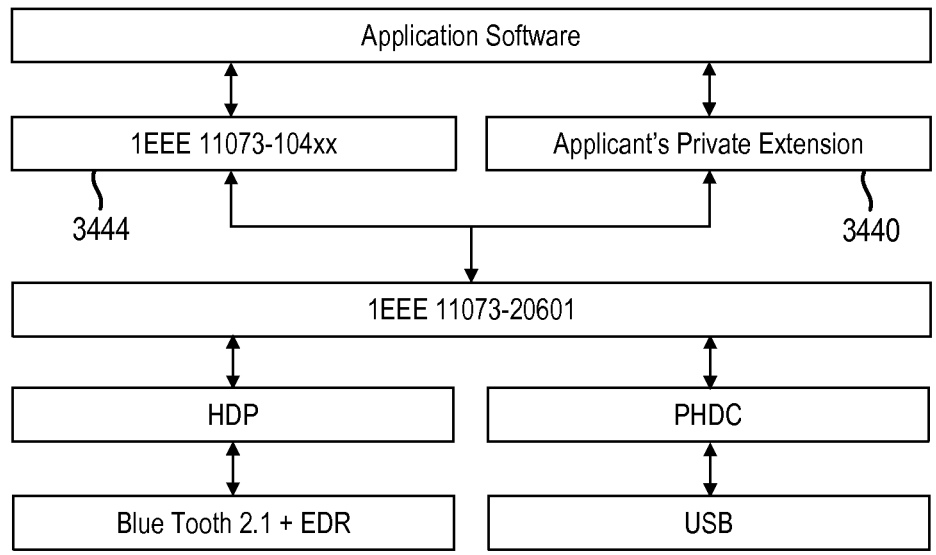
FIG. 14 is a block diagram depicting how applicant's private extension relates to the standardized communication protocols.

With reference to FIG. 14, this disclosure defines an extension 3440 to these configurations, i.e., applicant's private extension, which is not published in any of the ISO/IEEE 11073-104xx device specializations 3444. Applicant's private extension 3440 relationship to the standardized communication protocols is shown in FIG. 14. Generally speaking, implementation of this private extension 3440 defines the attributes and services to support the transfer and execution of specific commands and data. A basic framework for the private extension is first described below. Within this framework, a set of action commands that support structured collection procedures are then presented by this disclosure. The set of action commands are used by the configuration application 3452 and the collection interface 3456 to access and manipulate the parameters of structured collection procedures. It is readily understood that other types of commands sets can also fall within the framework for the private extension.

In an exemplary embodiment of applicant's private extension, each agent device has one MDS object. This top-level MDS object is instantiated from the MDS class. The MDS object represents the identification and status of the agent through its attributes. Beyond the class definition provided by the IEEE standards, additional standardized classes may be supported by the agents and managers in accordance with applicant's private extension. The additional standardized classes are referred to herein as RPC classes. RPC private nomenclature codes are assigned from the manufacturer-specific range of private term codes (0xF000-0xFBFF) within the object oriented partition category (MDC_PART-OBJ). The partition number for object oriented classes and objects is 1.

The attributes for each RPC class are defined in tables that specify the name of the attribute, its value and its qualifier. The qualifiers mean M—attribute is mandatory, C—attribute is conditional and depends on the condition stated in the remark or value column, R—attribute is recommended, NR—attribute is not recommended, and O—attribute is optional. Mandatory attributes shall be implemented by an agent. Conditional attributes shall be implemented if the condition applies and may be implemented otherwise. Recommended attributes should be implemented by the agent. Not recommend attributes should not be implemented by the agent. Optional attributes may be implemented on an agent.

RPC classes that instantiate numeric type objects are created as they exist in the device. These numeric type objects represent additional result data that can be obtained from the device in the same manner they are obtained from the device specialization. These objects shall be added to the device attribute value map for authenticated managers. Furthermore, applicant's private extension has defined a few RPC numeric objects available to system designers.

Applicant's private extension further defines an application protocol data unit as set forth below. An APDU represents the top-level message frame of the personal health device protocol. The extended APDU is added as an extension to the standard list of APDUs defined in the ISO/IEEE 11073-20601 specification.

```
Apdu Type ::=CHOICE {
  aarg [57856] AarqApdu, -- Association Request [0xE200]
  aare [58112] AareApdu, -- Association Response [0xE300]
  rlrq [58368] RlrqApdu, -- Association Release Request [0xE400]
  rlre [58624] RlreApdu, -- Association Release Response [0xE500]
  abrt [58880] AbrtApdu, -- Association Abort [0xE600]
  prst [59136] PrstApdu, -- Presentation APDU [0xE700]
  prrp [61440] PrrpApdu — applicant's extended APDU [0xF000]
}
```

A presentation APDU as defined in ISO/IEEE 11073-20601 is simply an octet string. Applicant's extended APDU adds a 16-bit CRC in order to ensure data integrity beyond the level provided by the transport and the ISO/IEEE 11073-20601 concept of reliable data channels. With this CRC, corrupted data can be detected by the application. This CRC covers the entire "RPC" part of the command invoke and command response APDUs.

```
PrrpApdup ::= SEQUENCE {
  data  OCTET STRING, (ENCODED VERSION OF DataApdu)
  crc   INT-U16 (checksum over the entire data field)
}
```

Applicant's extended APDU shall encapsulate unconfirmed Action Argument and confirmed Event Report Data APDUs defined by the ISO/IEEE 11073-20601 standard as follows:

```
ActionArgument Simple ::= SEQUENCE {
  obj-handle HANDLE
  action-type OID-Type,  --From the nom-part-obj partition
                         --Subpartition ACT (MDC_ACT_*)
  Action-info-args ANY DEFINED BY action-type
}

EventReportArgumentSimple ::=SEQUENCE {
  obj-handle HANDLE
  event-time Relative Time,
  event-type OID-Type    --From the nom-part-obj partition
                         --Subpartition NOTI (MDC_NOTI_*)
  event-info ANY DEFINED BY event-type
}
```

The approach used to invoke applicant's defined commands is to extend the MDS object methods with applicant defined actions. The ISO/IEEE 11073-20601 unconfirmed action service uses the ActionArgumentSimple structure previously discussed in this disclosure.

For the purposes of this specification, the fields would have the following values:

| | |
|---|---|
| handle | 0 (for the MDS object) |
| action-type | manufacturer specific code for applicant defined actions |
| action-info-args | manufacturer specific structure for each applicant defined action |

In order to invoke an applicant defined command, a manager would populate the action-type and action-info-arts of the ActionArgumentSimple object as follows:

| | |
|---|---|
| action-type | MDC_ACT_RPC_COMMAND_INVOKE |
| action-info-args | RpcCommandArguments |

The data objects used for command invocation action-info-args are defined as follows:

```
RpcCommandArguments ::=SEQUENCE {
  cmd-subcmd  INT-U16; //Command/subcommand combined
  arguments   RpcDataArguments [ ];
}
RpcDataArguments ::=SEQUENCE {
  type  INT-U16;
  data  ANY DEFINED BY type
}
```

The encoding of ANY DEFINED BY is defined in ISO/IEEE 11073-20601 as follows: The ANY DEFINED BY type (ASN.1 1988/90) or the instance-of type (ASN.1 1994) is encoded by a header of a length field to specify the number of octets in the encoding of the selected value that follows. The length element shall be expressed as the number of bytes (octets) contained in the value element. An empty argument shall be indicated with the type element set to RPC_ARG_TYPE_EMPTY, the length element set to 2 and the value element set to zero as an INT-U16. An RpbCommandArguments structure which contains a cmd-subcmd value that requires no arguments will include a single RpcDataArguments element indicating an empty argument.

The approach used to return data as a result of an applicant defined command invocation is to extend the MDS event reports with applicant defined events. The ISO/IEEE 11073-20601 confirmed notification service uses the EventReportArgumentSimple structure previously discussed in this disclosure. For the purposes of the specification, the fields would have the following values:

| | |
|---|---|
| Handle | 0 (for the MDS object) |
| event-time | 0 (event time is not used for applicant actions) |
| event-type | manufacturer specific code for applicant defined command responses. — |
| event-info | manufacturer specific structure for each applicant defined response. |

In order to respond to an applicant defined command, an agent would populate the event-type and event-info of the EventReportArgumentSimple object as follows:

| | |
|---|---|
| Event-type | MDC_NOTI_RPC_COMMAND_RESPONSE |
| event-info | RpcDataArguments [ ] |

The RpcDataArguments object is the same as is defined for applicant defined actions.

Methods (actions) available for the MDS object are defined in the table below. These methods are invoked using the ACTION service. In the table, the Method/Action column defines the name of the method. The Mode column defines whether the method is invoked as an unconfirmed action (i.e., roiv-cmip-action) or a confirmed action (i.e., roiv-cmip-confirmed-action). The Action-type column defines the nomenclature ID to use in the action-type field of an action request and response. The action-info-args column defines the associated data structure to use in the action message for the action-info-args field of the request. The Resulting action-info-args column define the structure to use in the action-info-args of the response.

| Method/Action | Mode | Action-type | Action-info-args | Resulting action-info-args |
|---|---|---|---|---|
| RPC-Command-Invoke | Unconfirmed | MDC_ACT_RPC_COMMAND_INVOKE | RpcCommandArguments | n/a |

This method allows the manager to invoke an applicant defined system command.

Potential events sent by the RPC object are defined in the table below. A manager shall support all methods defined in the table.

| Method/Action | Mode | Event-type | Event-info Parameter | Event-reply-info |
|---|---|---|---|---|
| RPC-Data-Event | Confirmed | MDC_NOTI_rpc_COMMAND_RESPONSE | RpcDataArguments | RpcDataArguments |
| RPC-Error-Event | Confirmed | MDC_NOTI_RPC_ERROR_RESPONSE | RpcDataArguments | RpcDataArguments |

For the command response event, after the execution of an applicant defined command has been requested via the ACTION service, the agent will process the command, sub-command and parameter objects. If there are no command parameter errors, the result will be an agent-initiated event report reflecting the result of successful command processing. In the case of command success, the event report will contain a command-specific result string of data as defined by this specification.

For the error response event, after the execution of an applicant defined command has been requested via the ACTION service, the agent will process the command, sub-command and parameter objects. If there are parameter errors, the result will be an agent-initiated event report specifying the parameter error. If a manager receives an RPC_ERR_HARDWARE or RPC_ERR_APPLICATION response, the manager should invoke the RPC Read and Clear Status command to retrieve further error information available from the device.

Within this framework, a set of action commands that support structured collection procedures is further described below. For example, a structured collection procedure is readable by using a Read ST Configuration command in conjunction with the subcommands listed in this section. The command for reading ST configuration is RPC_CMD_READ_ST_CONFIGURATION and has a value of 0x8000. It must be "OR-ed" with one of the read ST configuration subcommand values to form a complete command-subcommand value. Five exemplary subcommands are set forth below.

First, the Read 3-Day Reminders is a command that return an array of ST Reminder structures, the number of ST Reminder structures returned is device dependent. The ID values for the returned structures shall be one of Before Breakfast, Before Lunch, Before Dinner or Before Bedtime. An exemplary command definition is as follows.

Command/Subcommand = 0x8001
Input parameters: None
Output parameters: Reminder Array[ ] RpcStReminder (section 6.1.2.8)

RPC Command Invocation:

| | |
|---|---|
| cmd-subcmd | RPC_CMD_READ_ST_CONFIGURATION \| RPC_SUBCMD_READ_3D_REMINDERS |
| RpcDataArguments[0].type | RPC_ARG_TYPE_EMPTY |
| RpcDataArguments[0].length | 0x0002 |
| RpcDataArguments[0].value | 0x0000 |

RPC Command Response:

| | |
|---|---|
| obj-handle | 0x0000 |
| event-time | 0x0000 |
| event-type | MDC_NOTI_RPC_COMMAND_RESPONSE |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| o | o |
| o | o |
| o | o |
| RpcDataArguments[n].type | RPC_ARG_TYPE_ST_REMINDER |
| RpcDataArguments[n].length | Length of RpcStReminder structure in bytes |
| RpcDataArguments[n].value | RpcStReminder structure |

Second, the Read 3-Day Status is a command shall return an unsigned integer value which indicates whether the activation status is enabled or disabled. An exemplary command definition is as follows.

Command/Subcommand = 0x8002
Input parameters: None
Output parameters: Activation Status
OperationalState (See ISO/IEEE 11073-20601)

RPC Command Invocation:

| | |
|---|---|
| cmd-subcmd | RPC_CMD_READ_ST_CONFIGURATION \| RPC_SUBCMD_READ_3D_STATUS |
| RpcDataArguments[0].type | RPC_ARG_TYPE_EMPTY |
| RpcDataArguments[0].length | 0x0002 |
| RpcDataArguments[0].value | 0x0000 |

-continued

| | |
|---|---|
| RPC Command Response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_OPERATIONAL_STATE |
| RpcDataArguments[0].length | 0.0002 |
| RpcDataArguments[0].value | 0x0001 = disabled<br>0x0002 = enabled |

Third, the Read 3-Day Protocol is a command that returns: the Start Date value of the protocol as an RPC Date structure; the Pre-Meal Target Range value of the protocol as an RPC Target Range structure; the Post-Meal Target Range value of the protocol as an RPC Target Range structure; the Bedtime Target Range value of the protocol as an RPC Target Range structure. An exemplary command definition is as follows.

| | |
|---|---|
| Command/Subcommand = 0x8003 | |
| Input parameters: None | |
| Output parameters: | |
| Start Date | RpcTime |
| Pre-meal Target Range | RpcTargetRange |
| Post-meal Target Range | RpcTargetRange |
| Bedtime Target Range | RpcTargetRange |
| RPC Command Invocation: | |
| cmd-subcmd | RPC_CMD_READ_ST_CONFIGURATION \| RPC_SUBCMD_READ_3D_PROTOCOL |
| RpcDataArguments[0].type | RPC_ARG_TYPE_EMPTY |
| RpcDataArguments[0].length | 0x0002 |
| RpcDataArguments[0].value | 0x0000 |
| RPC Command response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_DATE |
| RpcDataArguments[0].length | Length of RpcDate structure in bytes |
| RpcDataArguments[0].value | RpcDate = start date value |
| RpcDataArguments[1].type | RPC_ARG_TYPE_TARGET_RANGE |
| RpcDataArguments[1].length | Length of RpcTargetRange structure in bytes |
| RpcDataArguments[1].value | RpcTargetRange = Pre-meal target range |
| RpcDataArguments[2].type | RPC_ARG_TYPE_TARGET_RANGE |
| RpcDataArguments[2].length | Length of RpcTargetRange structure in bytes |
| RpcDataArguments[2].value | RpcTargetRange = Post-meal target range |
| RpcDataArguments[3].type | RPC_ARG_TYPE_TARGET_RANGE |
| RpcDataArguments[3].length | Length of RpcTargetRange structure in bytes |
| RpcDataArguments[3].value | RpcTargetRange = Bedtime target range |

Fourth, the Read BIT Reminders is a command that shall return an array of ST Reminder structures. The number of ST Reminder structures returned is device dependent. The ID values for the returned structures shall be one of Administration or Acquisition. An exemplary command definition is as follows.

| | |
|---|---|
| Command/Subcommand = 0x8004 | |
| Input parameters: None | |
| Output parameters: Reminder Array[ ] RpcStReminder (section 6.1.2.8) | |
| RPC Command Invocation: | |
| cmd-subcmd | RPC_CMD_READ_ST_CONFIGURATION \| RPC_SUBCMD_READ_BIT_REMINDERS |
| RpcDataArguments[0].type | RPC_ARG_TYPE_EMPTY |
| RpcDataArguments[0].length | 0x0002 |
| RpcDataArguments[0].value | 0x0000 |
| RPC Command Response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| o | o |
| o | o |
| o | o |
| RpcDataArguments[n].type | RPC_ARG_TYPE_ST_REMINDER |
| RpcDataArguments[n].length | Length of RpcStReminder structure in bytes |
| RpcDataArguments[n].value | RpcStReminder structure |

Fifth, the Read BIT Status is a command that returns an unsigned integer value which indicates whether the activation status is enabled or disabled; and the Exit Reason value as a 16 bit enumeration. An exemplary command definition is as follows.

| | |
|---|---|
| Command/Subcommand = 0x8005 | |
| Input parameters: None | |
| Output parameters: | |
| Activation Status | OperationalState (See ISO/IEEE 11073-20601 |
| Exit Reason | UINT-16 |
| RPC Command Invocation: | |
| cmd-subcmd | RPC_CMD_READ_ST_CONFIGURATION \| RPC_SUBCMD_READ_BIT_STATUS |
| RpcDataArguments[0].type | RPC_ARG_TYPE_EMPTY |
| RpcDataArguments[0].length | 0x0002 |
| RpcDataArguments[0].value | 0x0000 |
| RPC Command Response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_OPERATIONAL_STATE |
| RpcDataArguments[0].length | 0.0002 |

-continued

| | |
|---|---|
| RpcDataArguments[0]. value | 0x0001 = disabled<br>0x0002 = enabled |
| RpcDataArguments[1]. type | RPC_ARG_TYPE_UINT16 |
| RpcDataArguments[1]. length | 0.0002 |
| RpcDataArguments[1]. value | Exit reason value |

This command shall return an array of RpcStParameter structures, comprised of the following parameters:
1. The Start Date value of the protocol as an RPC Date structure.
2. The Start Dosage value (IU) of the protocol as an 8 bit unsigned integer.
3. The Maximum Dosage value (IU) of the protocol as an 8 bit unsigned integer.
4. The Minimum Fasting Time value (number of hours) as an 8 bit unsigned integer.
5. The Maximum Use Time value (number of days) as an 8 bit unsigned integer.
6. The Completion Threshold value (mg/dL) of the protocol as a 16 bit unsigned integer.
7. The Severe Hypo Threshold value (mg/dL) of the protocol as a 16 bit unsigned integer.
8. The Hypo Threshold value (mg/dL) of the protocol as a 16 bit unsigned integer.
9. The Maximum Severe Hypo Events value of the protocol as an 8 bit unsigned integer.
10. The Maximum Hypo Events value of the protocol as an 8 bit unsigned integer.
11. The Maximum Violation Events value of the protocol as an 8 bit unsigned integer.
12. The Maximum Adherence Events value of the protocol as an 8 bit unsigned integer.
13. The Doctor Phone Number value of the protocol as an Octet String of even length.
14. The Daylight Saving Time status value of the protocol as a 16 bit enumeration value (see section 6.1.1.18 for enumeration values).
15. The Minimum Period Length value (days) of the protocol as an 8 bit unsigned integer.
16. The Number of Primary Samples as an 8 bit unsigned integer.

An exemplary command definition is as follows.

| | |
|---|---|
| Command/Subcommand = 0x8006 | |
| Input parameters: None | |
| Output parameters: Parameter Array[ ] RpcStParameter | |
| RPC Command Invocation: | |
| cmd-subcmd | RPC_CMD_READ_ST_CONFIGURATION \|<br>RPC_SUBCMD_READ_BIT_PROTOCOL |
| RpcDataArguments[0]. type | RPC_ARG_TYPE_EMPTY |
| RpcDataArguments[0]. length | 0x0002 |
| RpcDataArguments[0]. value | 0x0000 |
| RPC Command Response: | |
| obj-handle | 0x0000 |
| event-time | 0x0000 |
| event-type | MDC_NOTI_RPC_COMMAND_RESPONSE |
| RpcDataArguments[0]. type | RPC_ARG_TYPE_ST_PARAMETER |
| RpcDataArguments[0]. length | Length of RpcStParameter structure in bytes |
| RpcDataArguments[0]. value | RpcStParameter = parameter ID and value |
| o | o |
| o | o |
| o | o |
| RpcDataArguments[n]. type | RPC_ARG_TYPE_ST_PARAMETER |
| RpcDataArguments[0]. length | Length of RpcStParameter structure in bytes |
| RpcDataArguments[0]. value | RpcStParameter = parameter ID and value |

The parameters of a structure collection procedure can be changed by using the Set ST Configuration command in conjunction with the subcommands listed in this section. The command for setting ST configuration is RPC_CMD_SET_ST_CONFIGURATION and has a value of 0x8100. It must be "OR-ed" with one of the change setup subcommand values to form a complete command-subcommand value. Six exemplary subcommands are set forth below.

First, the Set 3-Day Reminders command shall set 3-Day time reminder values of the device to the values specified. The input parameter is an array of Structured Test time reminder structures. An agent device shall ignore any structures for which it has no corresponding ID. The ID values for the structures shall be one of Before Breakfast, Before Lunch, Before Dinner or Before Bedtime. The command returns an error code indicating success (RPC_ERR_NO_ERRORS) or failure. An exemplary command definition is as follows.

| | |
|---|---|
| Command/Subcommand = 0x8101 | |
| Input parameters: | |
| Reminder Array [ ] | RpcStReminder (section 6.1.2.8) |
| Output parameters: | |
| Error Code | Number |
| RPC Command Invocation: | |
| cmd-subcmd | RPC_CMD_SET_ST_CONFIGURATION \|<br>RPC_SUBCMD_SET_3D_REMINDERS |
| RpcDataArguments[0]. type | RPC_ARG_TYPE_ST_REMINDER |
| RpcDataArguments[0]. length | Length of RpcStReminder structure in bytes |
| RpcDataArguments[0]. value | RpcStReminder structure |
| o | o |
| o | o |
| o | o |
| RpcDataArguments[n]. type | RPC_ARG_TYPE_ST_REMINDER |
| RpcDataArguments[n]. length | Length fo RpcStReminder structure in bytes |
| RpcDataArguments[n]. value | RpcStReminder structure |
| RPC Command Response: | |
| obj-handle | 0x0000 |
| event-time | 0x0000 |
| event-type | MDC_NOTI_RPC_COMMAND_RESPONSE |

Second, the Set 3-Day Status command shall set the 3-Day Activation status value of the device to the value specified. The input parameters is a 16 bit OperationalState value. The command returns an error code indicating success (RPC_ERR_NO_ERRORS) or failure. An exemplary command definition is as follows.

| | |
|---|---|
| Command/Subcommand = 0x8102 | |
| Input parameters: | |
| Activation Status<br>(See ISO/IEEE 11073-20601) | OperationalState |
| Output parameters: | |
| Error Code | Number |
| RPC Command<br>Invocation: | |
| cmd-subcmd | RPC_CMD_SET_ST_CONFIGURATION \|<br>RPC_SUBCMD_SET_3D_STATUS |
| RpcDataArguments[0].<br>type | RPC_ARG_TYPE_OPERATIONAL_STATE |
| RpcDataArguments[0].<br>length | 0x0002 |
| RpcDataArguments[0].<br>value | 0x0001 = disabled<br>0x0002 = enabled |
| RPC Command<br>Response: | |
| obj-handle | 0x0000 |
| event-time | 0x0000 |
| event-type | MDC_NOTI_RPC_COMMAND_RESPONSE |
| RpcDataArguments[0].<br>type | RPC_ARG_TYPE_UINT16 |
| RpcDataArguments[0].<br>length | 0x0002 |
| RpcDataArguments[0].<br>value | Error code enumeration value |

Third, the Set 3-Day Protocol command shall set the following protocol values of the device to the values specified:

1. The Start Date value of the protocol as an RPC Date structure.
2. The Pre-Meal Target Range value of the protocol as an RPC Target Range structure.
3. The Post-Meal Target Range value of the protocol as an RPC Target Range structure.
4. The Bedtime Target Range value of the protocol as an RPC Target Range structure.

An exemplary command definition is as follows.

| | |
|---|---|
| Command/Subcommand = 0x8103 | |
| Input parameters: | |
| Start Date | Rpc Time |
| Pre-meal Target Range | Rpc Target Range |
| Post-meal Target Range | Rpc Target Range |
| Bedtime Target Range | Rpc Target Range |
| Output parameters: | |
| Error Code | Number |
| RPC Command<br>Invocation: | |
| cmd-subcmd | RPC_CMD_SET_ST_CONFIGURATION \|<br>RPC_SUBCMD_SET_3D_PROTOCOL |
| RpcDataArguments[0].<br>type | RPC_ARG_TYPE_DATE |
| RpcDataArguments[0].<br>length | Length of RpcDate structure in bytes |
| RpcDataArguments[0].<br>value | RpcDate = start date value |
| RpcDataArguments[1].<br>type | RPC_ARG_TYPE_TARGET_RANGE |

-continued

| | |
|---|---|
| RpcDataArguments[1].<br>length | Length of RpcTargetRange structure in bytes |
| RpcDataArguments[1].<br>value | RpcTargetRange = Pre-meal target range |
| RpcDataArguments[2].<br>type | RPC_ARG_TYPE_TARGET_RANGE |
| RpcDataArguments[2].<br>length | Length of RpcTargetRange structure in bytes |
| RpcDataArguments[2].<br>value | RpcTargetRange = Post-Meal target range |
| RpcDataArguments[3].<br>type | RPC_ARG_TYPE_TARGET_RANGE |
| RpcDataArguments[3].<br>length | Length of RpcTargetRange structure in bytes |
| RpcDataArguments[3].<br>value | RpcTargetRange = Bedtime target range |
| RPC Command<br>Response: | |
| obj-handle | 0x0000 |
| event-time | 0x0000 |
| event-type | MDC_NOTI_RPC_COMMAND_RESPONSE |
| RpcDataArguments[0].<br>type | RPC_ARG_TYPE_UINT16 |
| RpcDataArguments[0].<br>length | 0x0002 |
| RpcDataArguments[0].<br>value | Error code enumeration value |

Fourth, the Set BIT Reminders command shall set BIT time reminder values of the device to the values specified. The input parameter is an array of Structured Test time reminder structures. An agent device shall ignore any structures for which it has no corresponding ID. The ID values for the structures shall be one of Administration or Acquisition. The command returns an error code indicating success (RPC_ERR_NO_ERRORS) or failure. An exemplary command definition is as follows.

| | |
|---|---|
| Command/Subcommand = 0x8104 | |
| Input parameters: | |
| Reminder Array [ ] | RpcStReminder (section 6.1.2.8) |
| Output parameters: | |
| Error Code | Number |
| RPC Command<br>Invocation: | |
| cmd-subcmd | RPC_CMD_SET_ST_CONFIGURATION \|<br>RPC_SUBCMD_SET_BIT_REMINDERS |
| RpcDataArguments[0].<br>type | RPC_ARG_TYPE_ST_REMINDER |
| RpcDataArguments[0].<br>length | Length of RpcStReminder structure in bytes |
| RpcDataArguments[0].<br>value | RpcStReminder structure |
| o | o |
| o | o |
| o | o |
| RpcDataArguments[n].<br>type | RPC_ARG_TYPE_ST_REMINDER |
| RpcDataArguments[n].<br>length | Length of RpcStReminder structure in bytes |
| RpcDataArguments[0].<br>value | RpcStReminder structure |
| RPC Command<br>Response: | |
| obj-handle | 0x0000 |
| event-time | 0x0000 |
| event-type | MDC_NOTI_RPC_COMMAND_RESPONSE |
| RpcDataArguments[0].<br>type | RPC_ARG_TYPE_UINT16 |

| | |
|---|---|
| RpcDataArguments[0].<br>length | 0x0002 |
| RpcDataArguments[0].<br>value | Error code enumeration value |

Fifth, the Set BIT Status command shall set the following BIT status values of the device: the Activation Status value as a 16 bit OperationalState; and the Exit Reason value as a bit enumeration. The command returns an error code indicating success (RPC_ERR_NO_ERRORS) or failure. An exemplary command definition is as follows.

| | |
|---|---|
| Command/Subcommand = 0x8105 | |
| Input parameters: | |
| Activation Status<br>(See ISO/IEEE 11073-20601) | OperationalState |
| Exit Reason | UINT - 16 |
| Output parameters: | |
| Error Code | Number |
| RPC Command<br>Invocation: | |
| cmd-subcmd | RPC_CMD_SET_ST_CONFIGURATION \|<br>RPC_SUBCMD_SET_BIT_STATUS |
| RpcDataArguments[0].<br>type | RPC_ARG_TYPE_OPERATIONAL_STATE |
| RpcDataArguments[0].<br>length | 0x0002 |
| RpcDataArguments[0].<br>value | 0x0001 = disabled<br>0x0002 = enabled |
| RpcDataArguments[1].<br>type | RPC_ARG_TYPE_UINT16 |
| RPC Command<br>Response: | |
| obj-handle | 0x0000 |
| event-time | 0x0000 |
| event-type | MDC_NOTI_RPC_COMMAND_RESPONSE |
| RpcDataArguments[0].<br>type | RPC_ARG_TYPE_UINT16 |
| RpcDataArguments[0].<br>length | 0x0002 |
| RpcDataArguments[0].<br>value | Error code enumeration value |

Sixth, the Set BIT Protocol command shall set BIT protocol values of the device to the values specified. The input parameter is an array of Structured Test parameter structures. An agent device shall ignore any structures for which it has no corresponding parameter ID. The command returns an error code indicating success (PRC_ERR_NO_ERRORS) or failure. An exemplary command definition is as follows.

| | |
|---|---|
| Command/Subcommand = 0x8106 | |
| Input parameters: | |
| Reminder Array [ ] | RpcStParameter (section 6.1.2.9) |
| Output parameters: | |
| Error Code | Number |
| RPC Command<br>Invocation: | |
| cmd-subcmd | RPC_CMD_READ_ST_CONFIGURATION \|<br>RPC_SUBCMD_SET_BIT_PROTOCOL |
| RpcDataArguments[0].<br>type | RPC_ARG_TYPE_ST_PARAMETER |
| RpcDataArguments[0].<br>length | Length of RpcStParameter structure in bytes |
| RpcDataArguments[0].<br>value | RpcStParameter structure |
| o<br>o<br>o | o<br>o<br>o |
| RpcDataArguments[n].<br>type | RPC_ARG_TYPE_ST_PARAMETER |
| RpcDataArguments[n].<br>length | Length of RpcStParameter structure in bytes |
| RpcDataArguments[n].<br>value | RpcStParameter structure |
| RPC Command<br>Response: | |
| obj-handle | 0x0000 |
| event-time | 0x0000 |
| event-type | MDC_NOTI_RPC_COMMAND_RESPONSE |
| RpcDataArguments[0].<br>type | RPC_ARG_TYPE_UINT16 |
| RpcDataArguments[0].<br>length | 0.0002 |
| RpcDataArguments[0].<br>value | Error code enumeration value |

Power Management for a Handheld Medical Device

Referring now to FIG. 95, the communication module 3302 comprises a Bluetooth module 3600, a first communication module 3602, a second communication module 3604, a communication control module 3606, an arbitration module 3608, and an antenna switching module 3610. The Bluetooth module 3600 and the first communication module 3602 are integrated into an integrated circuit (IC) 3612. The Bluetooth module 3600 and the first communication module 3602 communicate in a 2.4 GHz frequency band (industrial, scientific, and medical or ISM band). The Bluetooth module 3600 and the first communication module 3602 share a first antenna 3614. The second communication module 3604 may operate in the ISM band or in a different frequency band and uses a second antenna 3616.

Specifically, the Bluetooth module 3600 communicates in the ISM band with the insulin pump 2914 or the PC 2906 via the first antenna 3614 using the Bluetooth protocol. The first communication module 3602 communicates in the ISM band with the CGM 2910 via the first antenna 3614 using the Gazell protocol. The second communication module 3604 communicates with other device 3618 using a wireless communication protocol different than Bluetooth and Gazell protocols. Throughout the present disclosure, the insulin pump 2914, the PC 2906, the CGM 2910, and related priorities are used as examples only. Additionally or alternatively, the Bluetooth module 3600 and the first and second communication modules 3602 and 3604 can communicate with other devices, and the other devices can have different priorities.

The communication control module 3606 controls communication of the diabetes manager 2904 with the other devices in the diabetes management system 2930 via the Bluetooth module 3600 and the first and second communication modules 3602 and 3604. The arbitration module 3608 arbitrates priority between the Bluetooth module 3600 and the first communication module 3602 when communication via the Bluetooth module 3600 and the first communication module 3602 is attempted concurrently. The antenna switching module 3610 switches the connection of the first antenna 3614 between the Bluetooth module 3600 and the first communication module 3602 depending on whether the Bluetooth module 3600 or the first communication module 3602 is granted priority.

Figure 18:
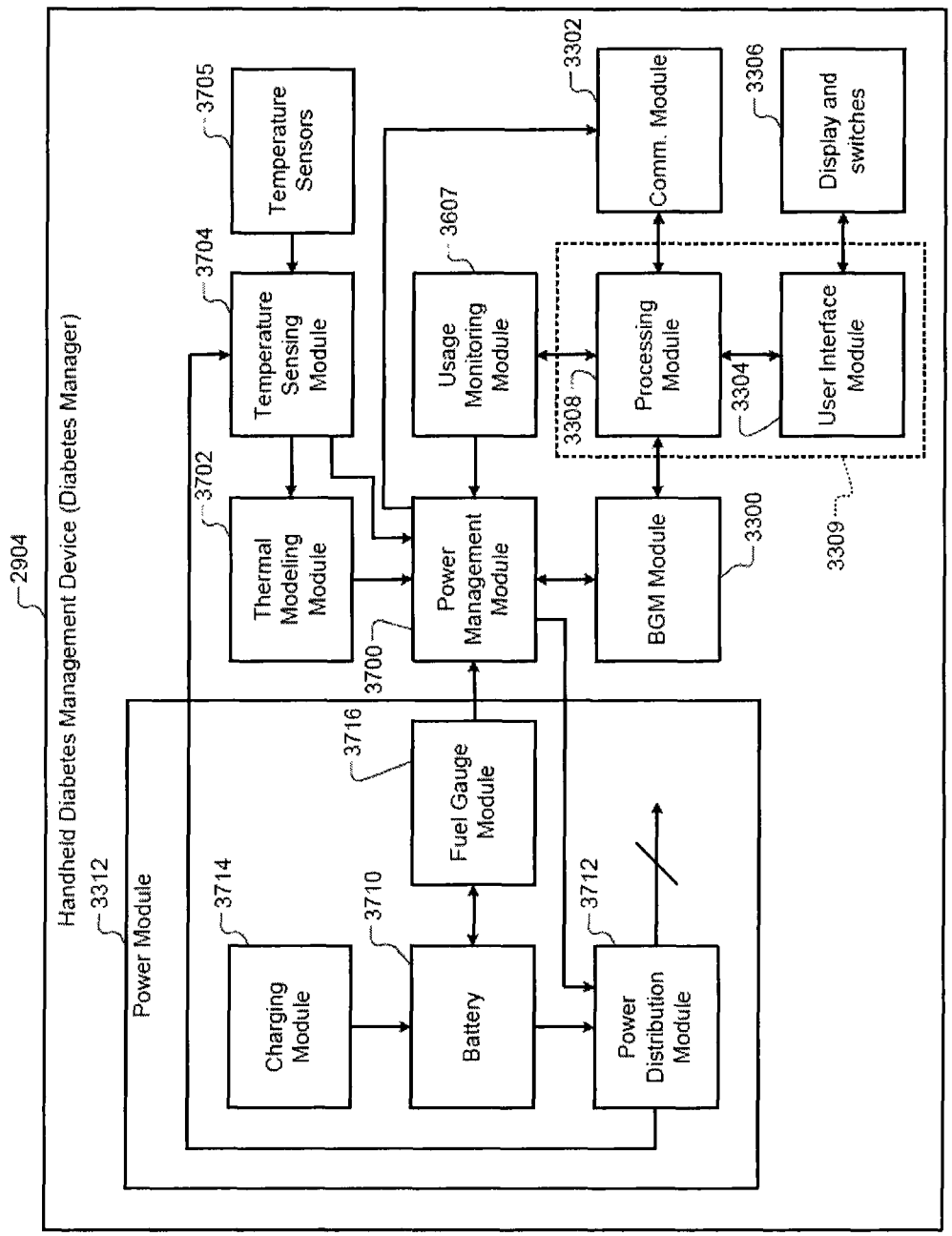
FIG. 18 is a detailed functional block diagram of the diabetes manager of FIG. 12.

Referring now to FIG. 18, a detailed functional block diagram of the diabetes manager 2904 is shown. Elements of the diabetes manager 2904 that are described above are not described again. In addition to these elements, the diabetes manager 2904 includes a power management module 3700, a thermal modeling module 3702, a temperature sensing module 3704, a plurality of temperature sensors 3705, and a usage monitoring module 3706. Further, the power module 3312 includes a rechargeable battery 3710, a power distribution module 3712, a charging module 3714, and a fuel gauge module 3716. The power distribution module 3712 selectively converts and distributes the power from the battery 3710 to the components of the diabetes manager 2904. The fuel gauge module 3716 determines the remaining capacity of the battery 3710. The charging module 3714 charges the battery 3710.

The power management module 3700 controls power consumption of the diabetes manager 2904 based on inputs received from the thermal modeling module 3702, the temperature sensing module 3704, the temperature sensors 3705, the usage monitoring module 3706, and the power module 3312. Based on these inputs, the power management module 3700 outputs power control signals to the power distribution module 3712. The power distribution module 3712 supplies power to the components of the diabetes manager 2904 based on the power control signals.

More specifically, the power distribution module 3712 receives power from the battery 3710 and generates different voltages and currents suitable for the different components of the diabetes manager 2904. The power distribution module 3712 outputs the voltages and currents (collectively power) to the components according to the power control signals received from the power management module 3700. Depending on the power control signals, the power distribution module 3712 can supply full power, no power, or standby power to one or more components. The components are activated when full power is supplied and deactivated when no power or standby power is supplied. For a plurality of standby modes, a plurality of intersecting sets of components may be activated to satisfy a plurality of device use cases.

Additionally, depending on the power control signals, the power distribution module 3712 can control frequencies of clock signals supplied to the components to conserve power. For example, a frequency of a clock signal supplied to a component when standby power is supplied to the component is less than the frequency when full power is supplied to the component. Use of clock signals having lower than normal frequencies requires less power than use of clock signals having normal clock frequencies, and this relationship scales linearly.

The temperature sensors 3705 are located at different locations in the diabetes manager 2904. The temperature sensors 3705 sense and output temperatures at the different locations to the temperature sensing module 3704. The temperature sensing module 3704 outputs the temperatures to the thermal modeling module 3702. The thermal modeling module 3702 processes the temperatures using a thermal model. Based on the processing, the thermal modeling module 3702 estimates an internal temperature of the diabetes manager 2904, a rate of change of the internal temperature, and an ambient temperature proximate to the blood glucose measurement strip 2936. The thermal model is described in U.S. patent application Ser. No. 12/479,212, filed Jun. 5, 2009, which is incorporated herein by reference in its entirety. The thermal model is also described below.

The temperature sensing module 3704 can also estimate the internal temperature and the rate of change of the internal temperature based on the amount of power supplied by the power distribution module 3712 to one or more components of the diabetes manager 2904. Specifically, the internal temperature of the diabetes manager 2904 and the rate of change of the internal temperature are directly proportional to the amount of power consumed by the components of the diabetes manager 2904. The power distribution module 3712 can provide data to the temperature sensing module 3704 indicating when and how long a component is activated and deactivated. Accordingly, the temperature sensing module 3704 can estimate the amount of heat generated by the component. Based on the estimates of heat generated by the components, the temperature sensing module 3704 can estimate the internal temperature and the rate of change of the internal temperature of the diabetes manager 2904.

The usage monitoring module 3706 monitors the usage of the diabetes manager 2904. For example, the usage can include, but is not limited to, one or more of these operations of the diabetes manager 2904: blood glucose measurement, interactions with the patient 2900 (e.g., receiving inputs, displaying data, generating alerts/alarms, etc.), communications with one or more devices external to the diabetes manager 2904 (e.g., receiving diagnostic data from the CGM 2910 or updates from the PC 2906, transmitting instructions to the insulin pump 2914, etc.), and so on. The usage monitoring module 3706 outputs the usage data to the power management module 3700. The usage data can also include data regarding planned or scheduled usage of one or more components of the diabetes manager 2904 (e.g., blood glucose measurement).

The power management module 3700 uses the usage data and the remaining capacity of the battery 3710 generated by the fuel gauge module 3716 to determine whether to activate or deactivate one or more components of the diabetes manager 2904. For example, when the remaining capacity of the battery is less than a predetermined threshold, the power management module 3700 generates the power control signals to deactivate components that consume large amount of power (e.g., the communication module 3302). Additionally, based on the usage data, the power management module 3700 can deactivate components that are idle (e.g., display) and/or that are not scheduled to be used for a predetermined period of time (e.g., the BGM module 3300).

The blood glucose measurements performed by the BGM module 3300 involve chemical analysis of the sample provided by the patient 2900 on a reaction site of the blood glucose measurement strip 2936. The chemical processes are sensitive to temperature. Since the port that receives the blood glucose measurement strip 2936 is proximate to the components of the diabetes manager 2904, the chemical processes at the reaction site can be affected by the internal temperature of the diabetes manager 2904. Accordingly, the blood glucose levels measured by the BGM module 3300 can be skewed by the internal temperature of the diabetes manager 2904.

In some blood glucose measurement strips, the chemical processes at the reaction site may be relatively insensitive to the internal temperature of the diabetes manager 2904. However, the accuracy of the blood glucose levels measured by the BGM module 3300 is characterized over a specified temperature range (e.g., 6° C. to 44° C.). The ambient temperature at the reaction site can be different than the internal temperature of the diabetes manager 2904 due to low thermal conductivity of the blood glucose measurement strip 2936. Accordingly, if the internal temperature of the diabetes manager 2904 is near 44° C. and is greater than the ambient temperature at the blood glucose measurement strip 2936, the BGM module 3300 may be prevented from measuring the blood glucose level (false positive). Conversely, if the ambient temperature at the blood glucose measurement strip 2936 is near 6° C. and is less than the internal temperature of the diabetes manager 2904, the BGM module 3300 may be permitted to measure the blood glucose level (false negative). These problems can be alleviated as follows.

The thermal modeling module 3702 estimates the ambient temperature proximate to the reaction site based on the internal temperature of the diabetes manager 2904. The power management module 3700 deactivates one or more components of the diabetes manager 2904 when the ambient temperature, the internal temperature, and/or the rate of change of internal temperature are greater than a predetermined threshold. The BGM module 3300 generates a status signal indicating whether a measurement is scheduled in a predetermined time or whether a measurement is in progress. For example, the status signal can indicate whether a measurement is scheduled at a particular time of the day. The status signal can also indicate a present status of the BGM module 3300 (e.g., whether the BGM module 3300 is performing a measurement or is idle). Based on the information conveyed by the status signal, the power management module 3700 can deactivate one or more components of the diabetes manager 2904 before or while the BGM module 3300 measures blood glucose levels. For example, the power management module 3700 can deactivate at least one or all of the communication modules 3600, 3602, and 3604 before or while the BGM module 3300 measures blood glucose levels.

Further, the diabetes manager 2904 can be configured to partially operate during charging of the battery 3710 depending on the state of charge of the battery 3710. For example, when the state of charge is greater than a first predetermined threshold, one or more of the communication modules 3600, 3602, and 3604 may be used to communicate with corresponding external devices (e.g., the insulin pump 2914, the PC 2906, and/or the CGM 2910). When the state of charge is greater than a second predetermined threshold, one or more of the user interfaces can be operated. For example, the display can operate at full brightness; the speaker can operate at full volume; and so on. When the state of charge is greater than a third predetermined threshold, the BGM module 3300 can be operated, and so on. These are only examples of sequences in which components of the diabetes manager 2904 can be operated during charging. Other sequences can be used.

The internal temperature of the diabetes manager 2904 can rise during charging of the battery 3710 and can remain high for a period of time after charging is complete. This could ordinarily skew and therefore prevent blood glucose measurements of the BGM module 3300. The power management module 3700, however, deactivates one or more components of the diabetes manager 2904 based on inputs received from the thermal modeling module 3702, temperature sensing module 3704, the temperature sensors 3705, and the usage monitoring module 3706 during charging of the battery 3710.

Accordingly, the internal temperature of the diabetes manager 2904 does not rise to a value that can skew the blood glucose measurements of the BGM module 3300. Further, the thermal modeling module 3702 estimates the ambient temperature proximate to the reaction site based on the internal temperature, and the BGM module 3300 adjusts blood glucose measurements based on the estimated ambient temperature. Alternatively, based on the estimated ambient temperature, the power management module 3700 can determine whether to permit the BGM module 3300 to measure blood glucose. Thus, the BGM module 3300 can reliably measure blood glucose levels during charging of the battery 3710 despite a rise in the internal temperature of the diabetes manager 2904.

The power management module 3700 can also forecast remaining operating time of the diabetes manager 2904 based on the remaining capacity of the battery 3710 received from the fuel gauge module 3716 and usage data received from the usage monitoring module 3706. The power management module 3700 can use the forecast to select components of the diabetes manager 2904 to deactivate. Further, the power management module 3700 can determine when and how long to deactivate the selected components. In some implementations, the power management module 3700 can also determine an order in which the selected components can be deactivated and reactivated. Thus, the power management module 3700 can use the forecast to prioritize and schedule power that can be supplied to one or more components of the diabetes manager 2904.

For example, based on the forecast, the power management module 3700 can output control signals to the arbitration module 3608, which can arbitrate priority between the Bluetooth module 3600 and the first communication module 3602 based on the control signals. When the control signals indicate that the remaining capacity of the battery 3710 is less than a predetermined threshold, the arbitration module 3608 can deny permission to one or more of the communication modules 3600, 3602, and 3604 that consume more power and grant priority to one of the communication modules 3600, 3602, and 3604 that consumes less power.

For example, the CGM 2910 monitors blood glucose more frequently than the insulin pump 2914 delivers insulin. Further, the first communication module 3602 communicates with the CGM 2910 more frequently than the frequency at which the Bluetooth module 3600 communicates with the insulin pump 2914. Further, the Bluetooth module 3600 may not communicate frequently with other devices such as the PC 2906. Consequently, the first communication module 3602 consumes more power than the Bluetooth module 3600. Accordingly, the power management module 3700 can deactivate the first communication module 3602 before deactivating the Bluetooth module 3600.

Further, when the control signals indicate that the remaining capacity of the battery 3710 is less than a predetermined threshold and an operation such as blood glucose measurement is scheduled to be performed, the power management module 3700 can reduce output levels of one or more of the user interfaces 3306 to conserve power until the battery 3710 is recharged. For example, brightness of the display and/or volume of the speaker can be limited to less than a predetermined threshold until the battery 3710 is recharged.

Figure 19A:
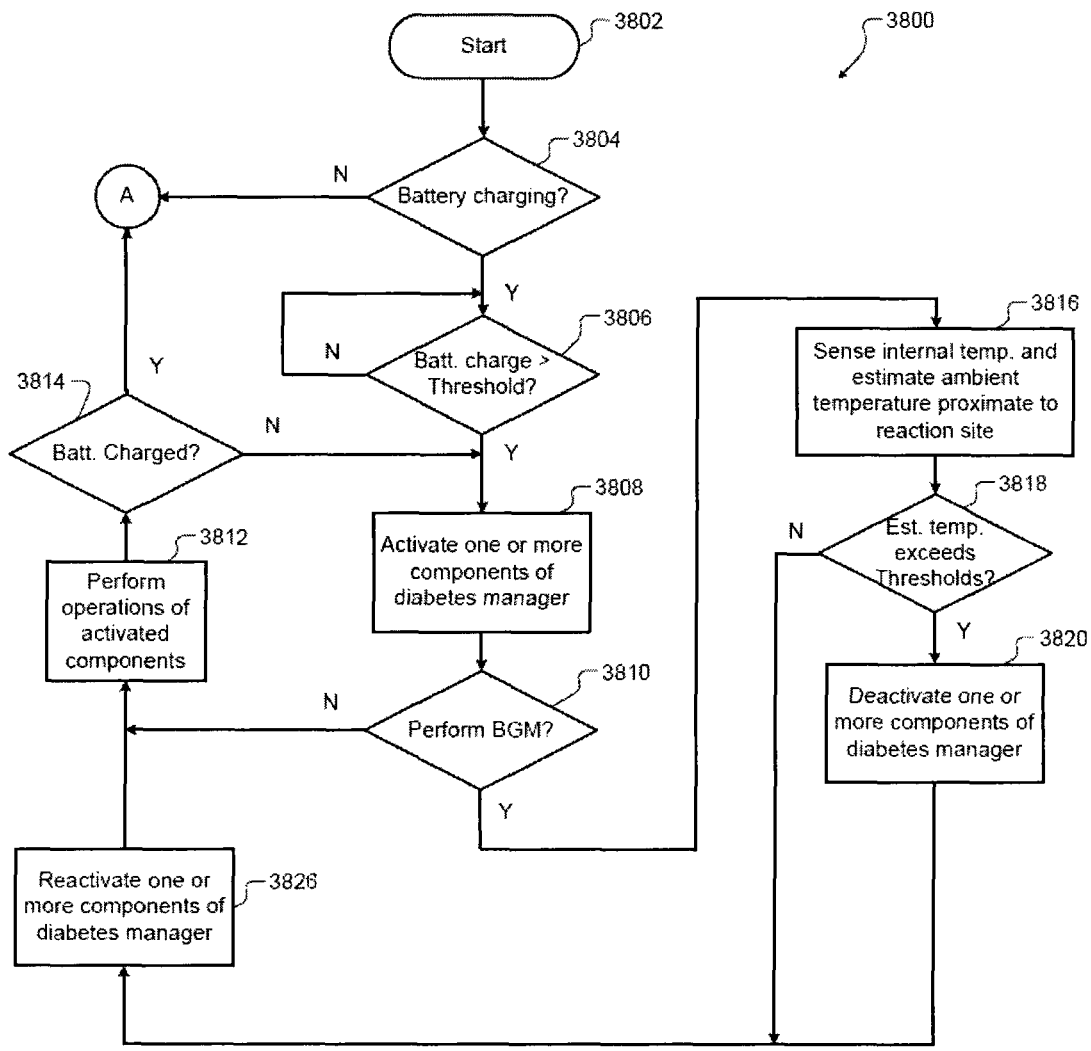
FIGS. 19A and 19B depict a flowchart of a method for managing power consumption of the diabetes manager and limiting effects of temperature on operations performed by the diabetes manager of FIG. 12.
Figure 19B:
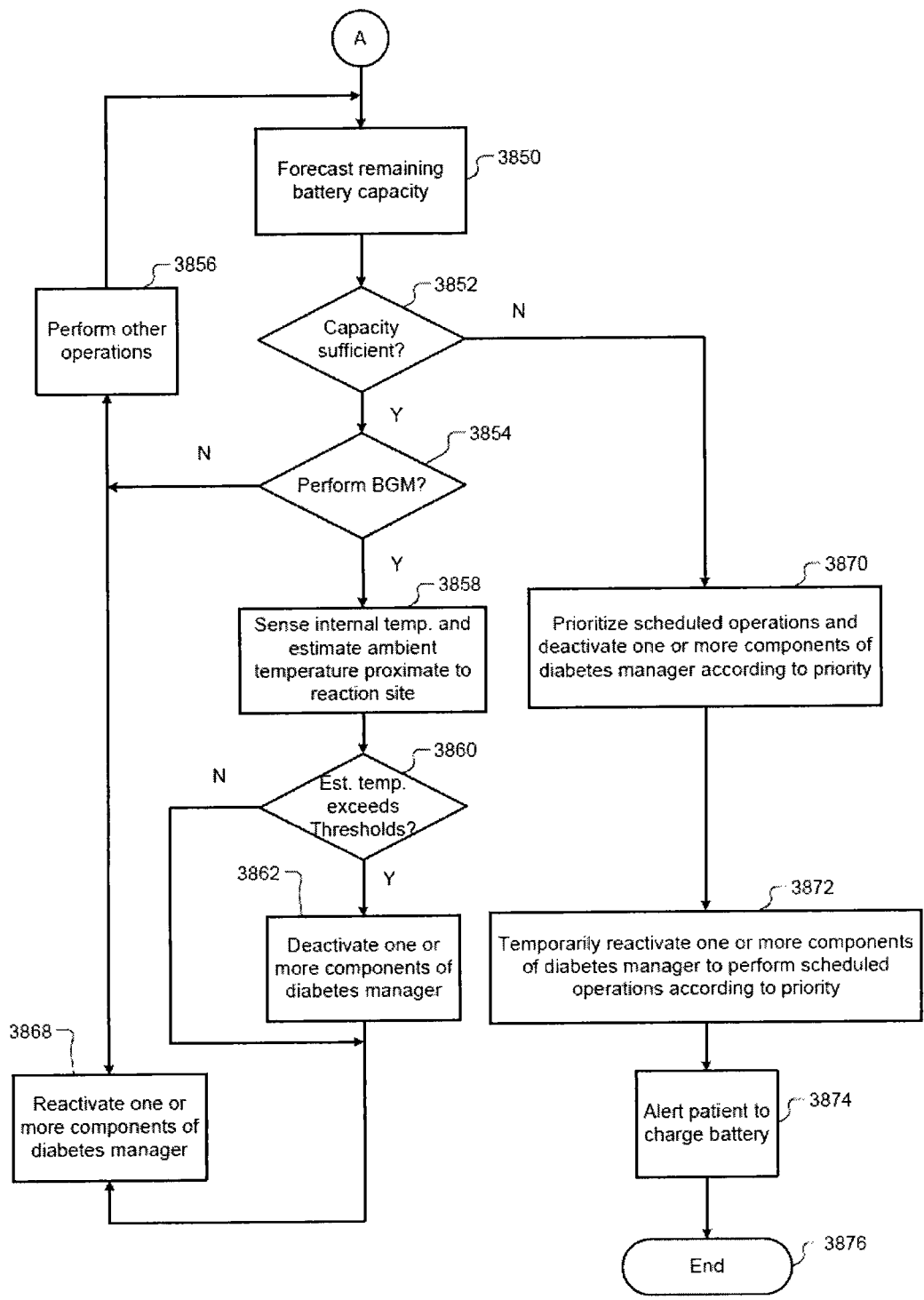

Referring now to FIGS. 19A and 19B, in an exemplary implementation, the power management module 3700 performs a method 3800. In FIG. 19A, control begins at 3802. At 3804, control determines if the battery 3710 is charging. If the battery 3710 is not charging, control goes to 3850 (see FIG. 19B). If the battery 3710 is charging, at 3806, control determines if the state of charge of the battery 3710 is greater than a predetermined threshold, which indicates that the battery 3710 has sufficient charge to supply power to one or more components of the diabetes manager 2904. Control waits until the state of charge of the battery 3710 is greater than a predetermined threshold. When the state of charge of the battery 3710 is greater than a predetermined threshold, at 3808, control activates one or more components of the diabetes manager 2904.

At 3810, control determines if a blood glucose measurement (BGM) is to be performed. If a BGM is not to be performed, at 3812, control performs operations of activated components. At 3814, control determines if the battery 3710 is charged. If the battery 3710 is charged, control goes to 3850 (see FIG. 19B). If the battery 3710 is not charged, control returns to 3808.

At 3816, if a BGM is to be performed, control senses the internal temperature of the diabetes manager 2904 and uses the thermal model to estimate the external temperature. At 3818, control determines if the estimated external temperature is greater than a first predetermined threshold or less than a second predetermined threshold. If either case is true, at 3820, control deactivates one or more components of the diabetes manager 2904. Thereafter, or if the estimated external temperature does not exceed the predetermined thresholds, at 3826, control reactivates one or more deactivated components, and control returns to 3812. In some implementations, instead of waiting for the temperature to return to an acceptable temperature range, the processing module 3308 can output a message to the patient 2900 that the temperature is outside the acceptable temperature range, and testing is disallowed.

In FIG. 19B, at 3850, control forecasts the remaining battery capacity as described above. At 3852, control determines if the remaining battery capacity is sufficient to perform scheduled operations. If the remaining battery capacity is sufficient to perform scheduled operations, at 3854, control determines if a blood glucose measurement (BGM) is to be performed. If a BGM is not to be performed, at 3856, control performs other scheduled operations of the diabetes manager 2904, and control returns to 3850.

At 3858, if a BGM is to be performed, control senses the internal temperature of the diabetes manager 2904 and uses the thermal model to estimate the external temperature. At 3860, control determines if the estimated external temperature is greater than a first predetermined threshold or less than a second predetermined threshold. If either case is true, at 3862, control deactivates one or more components of the diabetes manager 2904. Thereafter, or if the estimated external temperature does not exceed the predetermined thresholds, at 3868, control reactivates one or more deactivated components, and control returns to 3856. In some implementations, instead of waiting for the temperature to return to an acceptable temperature range, the processing module 3308 can output a message to the patient 2900 that the temperature is outside the acceptable temperature range, and testing is disallowed.

At 3870, if the remaining battery capacity is insufficient (e.g., less than a predetermined threshold) to perform scheduled operations, control prioritizes scheduled operations of the diabetes manager 2904 and deactivates one or more components of the diabetes manager 2904 according to the priority. Control also limits capabilities of one or more user interfaces 3306 (e.g., display, speaker, etc.) of the diabetes manager 2904. At 3872, control temporarily reactivates one or more deactivated components to perform the scheduled operations according to the priority, and deactivates the components after the scheduled operations are completed.

At 3874, control alerts the patient 2900 to charge the battery 3710, and control ends at 3876.

In summary, a system for managing the power consumption of diabetes manager 2904 and limiting effects of temperature on operations performed by the diabetes manager 2904 includes the BGM module 3300, the temperature sensing module 3704, and the power management module 3700. The BGM module 3300 selectively measures blood glucose in a blood sample and generates a status signal indicating a status of operation of the BGM module 3300. The temperature sensing module 3704 senses the internal temperature of the diabetes manager 2904. The power management module 3700 deactivates one or more components of the diabetes manager 2904 based on the status of operation of the BGM module 3300 when the internal temperature of the diabetes manager 2904 exceeds a threshold temperature.

In an alternative embodiment, the system includes a temperature sensor (e.g., 3705) that senses the internal temperature of the diabetes manager 2904 and a port that externally receives a removable measurement strip (e.g., 2936) having a reaction site for receiving a blood sample. The system further includes the thermal modeling module 3702 and the power management module 3700. The thermal modeling module 3702 uses a thermal model to estimate the ambient temperature proximate to the reaction site based on the internal temperature. The power management module 3700 deactivates one or more components of the diabetes manager 2904 when the ambient temperature proximate to the reaction site is greater than a first threshold temperature or is less than a second threshold temperature.

Stated generally, a system for managing power consumption of a handheld medical device (e.g., 2904) and limiting effects of temperature on operations performed by the handheld medical device includes a temperature sensor (e.g., 3705), a port, a thermal modeling module (e.g., 3702), and a power management module (e.g., 3700). The temperature sensor senses an internal temperature of the medical device. The port externally receives a removable measurement strip having a reaction site for receiving a sample of a substance for measuring a health parameter of a patient. The thermal modeling module uses a thermal model to estimate an ambient temperature proximate to the reaction site based on the internal temperature. The power management module deactivates one or more components of the medical device when the ambient temperature proximate to the reaction site is greater than a first threshold temperature or is less than a second threshold temperature.

The thermal model utilized by the thermal modeling module 3702 is now described. The thermal model provides a method for estimation of the temperature at a blood glucose (bG) test strip reaction site when the test strip (e.g., the glucose measurement strip 2936) may be at a different temperature than the bG measurement electronic circuitry (e.g., the BGM module 3300 or the diabetes manager 2904). The readings from the temperature sensor (e.g., the temperature sensors 3705) in the bG measurement circuitry are used by a temperature estimation algorithm to estimate the temperature at the bG test strip reaction site. It is important to know the temperature at the reaction site in order to avoid unwarranted over-temperature lockout conditions, or to ignore valid under-temperature lock-out conditions, that would prevent proper use of the bG meter. Since all but the base of the bG test strip is exposed to the ambient air, the reaction site temperature closely follows the ambient air temperature. Studies have confirmed that the test strip has low thermal conductivity, so the internal temperature of the BGM module may differ from the temperature of the reaction site on the test strip.

In its simplest form, the algorithm uses a reading from a temperature sensor as the estimate of the reaction site temperature. If the reading is changing at a rate that exceeds a specified threshold, the temperature estimation algorithm may obtain an improved estimate of the ambient air temperature, and hence the reaction site temperature, by amplifying those changes in the temperature sensor reading and formulating a new prediction based on a static thermal model of the bG measurement device.

The reading from the sensor can, however, change not due to changes in the ambient air, but rather due to the internal heating of electronic components inside the device containing the bG circuitry (e.g., the diabetes manager 2904). For example, consider the case of bG measurement circuitry installed in a cell phone. Due to the high operating temperature of circuitry inside the cell phone, the temperature readings from the temperature sensor may be unduly elevated. Furthermore, the internal heat generation may vary depending on how the cell phone is being used. Accurate temperature estimation must continue even when the thermal characteristics of the device change with specific usage.

The thermal model provides a method for estimating the temperature elevation due to any number of heat sources of arbitrary strength and arbitrary duration. Once the total expected temperature elevation has been determined, then this quantity can be subtracted from the temperature sensor reading to furnish a corrected temperature reading upon which an accurate ambient temperature prediction can be based. An advantage of this approach is that the thermal model can be dynamically adjusted depending on the specific usage of the device. As more functions are added to the device, it becomes increasingly important to estimate reaction site temperature based on how the device has been used prior to the bG test.

The mathematical method of the thermal mode relies upon the linear superposition of temperature responses to an applied heat source or sources. A time-varying heat source may be characterized as a series of heat "impulses" of varying magnitude. For the purposes of the present disclosure, an "impulse" is a period of heating lasting a short time as compared to the total duration of heating. Due to linear superposition, the temperature response of a heat source of extended duration can be found by adding up the temperature responses of a succession of impulses that represent that heat source.

Within a device there may be multiple sources of heat, generally caused by the internal heat generation of specific electronic components. Again by linear superposition, the total temperature response of all of these components may be found by summing their individual contributions. These heat sources may become active prior to or during a blood glucose measurement. Their effect on the temperature measurement must be accounted for.

A number of factors affect the temperature response to a given heat source. Within the device enclosure, the heat source may be located on the same circuit board as the temperature sensor or on another circuit board, and it may be near the sensor or far from it. The heat generation of a particular electronic component may vary greatly during its various modes of operation. This heating can be mathematically characterized. The corresponding temperature response at the temperature sensor can also be measured with reasonable accuracy. Depending on the location of the heat producing electronic component relative to the temperature sensor and the nature of the thermal pathways between them, the temperature response at the temperature sensor can vary a great deal. A heat source near the temperature sensor tends to produce a rapid rise in temperature after the heat is applied, followed by a rapid decline in temperature when the heat is removed. For a more distant heat source, the rise and fall in temperature are more gradual and more time elapses before the peak temperature is reached.

The method of linear superposition may be used to characterize the combined effect of multiple, time-varying heat sources in an electronic device, such as a hand-held device incorporating bG measurement circuitry (e.g., the diabetes manager 2904). Consider the case of a heat source "A" of strength Qa being applied for duration $(Na/2) \cdot \Delta t$, where Na is an even positive integer and $\Delta t$ is an increment of time. A temperature sensor is installed in the package at a different location than the heat source. Let the temperature elevation at the location of the temperature sensor at time $t_i = i \cdot \Delta t$ after the activation of the heat source be given by $Ea_i = (Ta_i - T_{ref})$ where $Ta_i$ is the temperature at the location of the temperature sensor at time $t_i$, and $T_{ref}$ is a suitable reference temperature.

Let the reference temperature be the ambient temperature of the electronic package: $T_{ref} = T_{amb}$. The temperature elevations Ea, for times $t_1$ through $t_{Na}$ can be expressed by the following matrix equation:

$$Qa \cdot \begin{bmatrix} 1 & 0 & \ldots & & 0 & 0 & \ldots & & 0 \\ 1 & 1 & 0 & \ldots & & 0 & 0 & \ldots & 0 \\ 1 & 1 & 1 & 0 & \ldots & 0 & 0 & \ldots & 0 \\ \ldots & & & & & \ldots & & & \\ 1 & \ldots & & 1 & 0 & 0 & \ldots & & 0 \\ 1 & 1 & \ldots & & 1 & 0 & \ldots & & \\ 0 & 1 & \ldots & & 1 & 1 & 0 & \ldots & 0 \\ 0 & 0 & 1 & \ldots & & 1 & 1 & 1 & 0 & \ldots & 0 \\ 0 & 0 & 0 & 1 & \ldots & 1 & 1 & 1 & 1 & 0 & \ldots & 0 \\ \ldots & & & & & \ldots & & & \\ 0 & \ldots & & 0 & 1 & 1 & \ldots & & 1 & 0 \\ 0 & 0 & \ldots & & 0 & 1 & 1 & \ldots & & 1 \end{bmatrix} \begin{bmatrix} A_1 \\ A_2 \\ \vdots \\ \vdots \\ \vdots \\ \vdots \\ \vdots \\ A_{Na} \end{bmatrix} = \begin{bmatrix} Ea_1 \\ Ea_2 \\ \vdots \\ \vdots \\ \vdots \\ \vdots \\ Ea_{Na} \end{bmatrix}$$

or $Qa \cdot [U] \cdot [A] = [Ea]$, where Qa is the magnitude of the heat source at point "A", [U] is the matrix of unit impulses, [A] is the matrix of impulse responses, and [Ea] is the matrix of temperature elevations.

If the magnitude Qa of the heat source and the temperature elevations from times $t_i$ through $t_{Na}$ are known, then the impulse responses $[A_i]$, $i=1$ to Na, can be determined. Likewise for a heat source at point "B" of strength Qb applied for duration $(Nb/2) \cdot \Delta t$, the temperature elevations Ebi for times $t_1$ through $t_{Nb}$ can be expressed by the following matrix equation $Qb \cdot [U] \cdot [B] = [Eb]$, where, Qb is the magnitude of the heat source at point "B", [U] is the matrix of unit impulses, [B] is the matrix of impulse responses, and [Eb] is the matrix of temperature elevations. Similarly, if the magnitude Qb of the heat sources and the temperature elevations from times $t_1$ through $t_{Nb}$ are known, then the impulse responses $[B_i]$, $i=1$ to Nb, can be found.

To characterize any given heat source "X" among those being considered, the total time duration $Nx \cdot \Delta t$ should be sufficiently long that for time $t > Nx \cdot \Delta t$, the magnitude of the impulse response is approximately zero, i.e., $xi \approx 0$ for $i > Nx$.

For the purposes of the thermal model, let Nx be an even number chosen such that either XNx−1>0 and Xi=0 for i>Nx−1 or XNx>0 and Xi=0 for i>Nx. In other words, Xi is truncated to zero for i>Nx. The interval Δt corresponds to the "impulse" interval, a suitably short interval of time over which a heat source of unit strength acts. The interval Δt should be small compared to the total duration over which the temperature elevations resulting from the applied heat source persist in the body of the electronic device.

For all heat sources of interest, let N be a number equal to the maximum of the individual interval counts Na, Nb, etc.: N≥max{Na, Nb, . . . }. Hence for any given heat source, the impulse response at time ti where i≤N may be zero:

$A_i \geq 0$ for $1 \leq i \leq Na$, $A_i = 0$ for $i > Na$, and $Na \leq N$;
$B_i \geq 0$ for $1 \leq i \leq Nb$, $B_i = 0$ for $i > Nb$, and $Nb \leq N$;

and so on for all heat sources. Thus chosen, the upper limit N on the interval counts will be sufficiently large that the matrix of impulse responses for each and every heat source may be characterized with minimal loss due to truncation.

To characterize the impulse responses of the various heat sources in an electronic device, a series of procedures may be performed, based on the process described above. For each heat source "X" (="A", "B", etc.), the following procedure may be followed:

1) Allow the device to come to equilibrium temperature with its environment. The ambient temperature is the reference temperature: $T_{ref} = T_{amb}$.
2) Activate heat source "X" at constant strength Qx for a duration of (N/2)·Δt, where N and Δt have been chosen in the manner described above (i.e., N≥max{Na, Nb, . . . } and Δt is a suitable impulse interval. Record the initial temperature at the temperature sensor at the time that the heat source is activated and the temperature at each succeeding time $t_i = i \cdot \Delta t$, i=1 to N/2.
3) At time t=(N/2)·Δt, deactivate the heat source "X" and continue recording the sensor temperature at times $t_i = i \cdot \Delta t$, i=(N/2)+1 to N.
4) Calculate the temperature elevation at each time step:

$$Ex_i = (Tx_i - T_{ref}), 0 \leq i \leq N$$

5) Using matrix methods, determine the matrix of impulse temperature responses, [Xi]:

$$Qx \cdot [U] \cdot [X] = [Ex]$$

$$[X] = (1/Qx) \cdot [U]^{-1} \cdot [Ex]$$

6) Repeat the above steps for each heat source of interest.

During the procedure, the ambient environment of the electronic device should be held to conditions representative of the environment in which the device is expected to be used. For example, if the device will spend most of its time in still air at room temperature, then these conditions should be maintained. If the operating environment is expected to be drafty, then a suitable airflow should be imposed. Once the impulse response matrices for all of the heat sources have been determined, then the principle of superposition can be applied to determine the expected temperature response of the device to the influence of any combination of these sources acting at arbitrary strengths and for arbitrary durations. The above discussion considered heat sources with constant magnitude.

Consider now a sequence of heat impulses from source k having duration Δt and variable magnitude $[Q_k]$ beginning at time N·Δt before the present:

$$[Q_k] = [Q_{k,1} Q_{k,2} \ldots Q_{k,N-1} Q_{k,N}]$$

where the magnitudes of the heat impulses are given by $Q_{k,1}$ is the magnitude at time $t = -N \cdot \Delta t$ $Q_{k,2}$ is the magnitude at time $t = -(N-1) \cdot \Delta t$ $\ldots$ $Q_{k,N-1}$ is the magnitude at time $t = -2 \cdot \Delta t$ $Q_{k,N}$ is the magnitude at time $t = -1 \cdot \Delta t$.

The temperature elevation $E_k$ due to this sequence of impulses from source k is given by:

$$E_k = \sum_{i=1}^{N} Q_{k,i} \cdot X_{k,N-i+1}$$

or $$E_k = \sum_{i=1}^{N} Q_{k,N-i+1} \cdot X_{k,i}$$

where $[X_k] = [X_{k,1} X_{k,2} \ldots X_{k,N-1} X_{k,N}]$ is the impulse temperature response for source k.

The total temperature elevation due to M sources is given by $$E_{total} = \sum_{k=1}^{M} E_k = \sum_{k=1}^{M} \sum_{i=1}^{N} Q_{k,N-i+1} \cdot X_{k,i}$$

Note that the effect of any temperature impulse prior to time −N·Δt is considered negligible and so no corresponding source terms are included in the calculations. This total temperature elevation due to the internal heat sources of the device may now be subtracted from the temperature sensor reading to yield a corrected temperature:

$$T_{corr} = T_{sensor} - E_{total}$$

The customary temperature estimation method may now be applied to this corrected temperature in order to obtain a prediction of the ambient temperature and, hence, the effective test strip reaction site temperature.

To implement the thermal model in a bG measurement device, the control for the device should know which components are being activated and at what strength and for how long. This information plus the reading of the temperature sensor mounted on the circuit board for the bG measurement circuitry is used to determine the temperature response to heat released by each of the heat generating components. Any number of these components may be characterized by the thermal model. The impulse response matrix for each component is stored with the temperature estimation algorithm and may be retrieved to calculate a temperature response whenever that component is activated.

The thermal model contains a number of operating parameters that need to be quantified. The maximum period of time that the temperature response due to an input of heat from any of the components is tracked is given by N·Δt, where N is the total number of samples and Δt is the sampling interval. From the standpoint of the algorithm, N is the total number of elements in the impulse temperature response matrix (dimension N×1) and Δt is the impulse duration. For a handheld electronic device (e.g., the diabetes manager 2904), this maximum period is on the order of one to two hours. By that time, virtually all of any generated heat will have been dissipated to the environment of the device. The sampling interval $\Delta t$, which is also the assumed impulse duration, should be small enough to resolve the time-varying temperature response from a transient heat release with a sufficient degree of precision that reasonably accurate estimates of the individual and total temperature elevations can be calculated.

For a handheld electronic device such as the diabetes manager 2904, a suitable sampling interval might be on the order of several seconds to a few minutes. The exact choice depends on the nature of the heat sources and the degree of precision desired. A sampling interval of one minute appears to provide adequate results for the devices that have been tested. For a maximum tracking period of one hour, a one minute sampling period would yield N=60 samples, and hence 60 elements in the impulse temperature response matrices for the various components. As a further refinement of the thermal model, if the heat being released by a particular component varies during a given sampling period, then the reported strength of that source (which is known by the electronic control) can be adjusted to give a representative average over the interval.

Coexistence of Multiple Radios in a Medical Device

Referring now to FIG. 9, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 10, the patient 2900 can use a continuous glucose monitor (CGM) 2910, an ambulatory non-durable insulin infusion pump 2912 or an ambulatory durable insulin infusion pump 2914 (hereinafter insulin pump 2912 or 2914), and the handheld diabetes management device 2904 (hereinafter the diabetes manager 2904). The CGM 2910 uses a subcutaneous sensor to sense and monitor the amount of glucose in interstitial fluid of the patient 2900 and communicates corresponding data to the diabetes manager 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives data from the CGM 2910 from which glucose levels of the patient 2900 are computed. The diabetes manager 2904 transmits instructions to the insulin pump 2912 or 2914, which delivers insulin to the patient 2900. Insulin can be delivered in a scheduled manner in the form of a basal dose, which maintains a predetermined insulin dose to the patient 2900. Additionally, insulin can be delivered in the form of a bolus dose, which raises the amount of insulin delivered to the patient 2900 by a predetermined amount.

Referring now to FIG. 11, a diabetes management system 2390 used by the patient 2900 and the clinician 2902 includes one or more of the following devices: the diabetes manager 2904, the continuous glucose monitor (CGM) 2910, the insulin pump 2912 or 2914, a mobile device 2932, the PC 2906 with the diabetes analysis software, and other healthcare devices 2934. The diabetes manager 2904 is configured as a system hub and communicates with the devices of the diabetes management system 2390. Alternatively, the mobile device 2932 can serve as the system hub. Communication between the devices in the diabetes management system 2390 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive glucose readings from one or more sources (e.g., from the CGM 2910). The CGM 2910 continuously monitors the glucose level of the patient 2900. The CGM 2910 periodically communicates data to the diabetes manager 2904 from which the diabetes manager 2904 computes glucose levels of the patient. The diabetes manager 2904 and the CGM 2910 communicate wirelessly using a proprietary wireless protocol. Throughout the present disclosure, Gazell wireless protocol developed by Nordic Semiconductor, Inc. is used as an example only. Any other suitable wireless protocol can be used instead. The Gazell wireless protocol is described in nRF24LE1 Ultra-low Power Wireless System On-Chip Solution, Product Specification v1.4, which is incorporated herein by reference in its entirety.

Additionally, the diabetes manager 2904 includes a blood glucose meter (BGM) and a port that communicates with the BGM (not shown). The port can receive a blood glucose measurement strip 2936. The patient 2900 deposits a sample of blood on the blood glucose measurement strip 2936. The BGM analyzes the sample and measures the blood glucose level in the sample. The blood glucose level measured from the sample and/or the glucose level computed using data received from the CGM 2910 can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with the other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 may use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2390 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2390. The configurator has a database to store configuration information of the diabetes manager 2904 and the other devices. The configurator can communicate with users through standard web or computer screens in non-web applications. The configurator transmits user-approved configurations to the devices of the diabetes management system 2390. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a pager, or a personal digital assistant (PDA). The diabetes manager 2904 can send messages to an external network through the mobile device 2932. The mobile device 2932 can transmit messages to the external network upon receiving requests from the diabetes manager 2904.

Referring now to FIG. 12, the diabetes manager 2904 comprises a blood glucose measuring (BGM) module 3300, a communication module 3302, a user interface module 3304, user interfaces 3306, a processing module 3308, memory 3310, and a power module 3312. The user interface module 3304 and the processing module 3308 can be implemented by an application processing module 3309. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices of the diabetes management system 2390. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The processing module 3308 outputs data to and receives data from the user interfaces 3306 via the user interface module 3304. The processing module 3308 outputs data to and receives data from the devices of the diabetes management system 2390 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

Figure 20A:
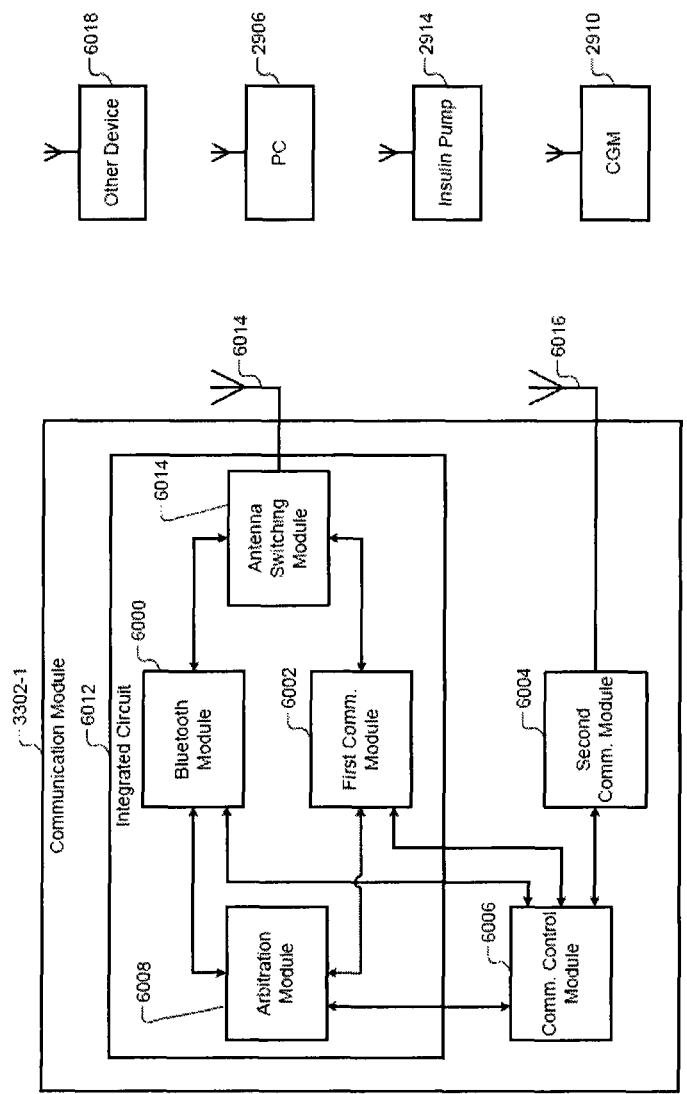
FIG. 20A is a functional block diagram of a communication module used by the diabetes manager of FIG. 12, where the communication module uses a shared antenna.
Figure 20B:
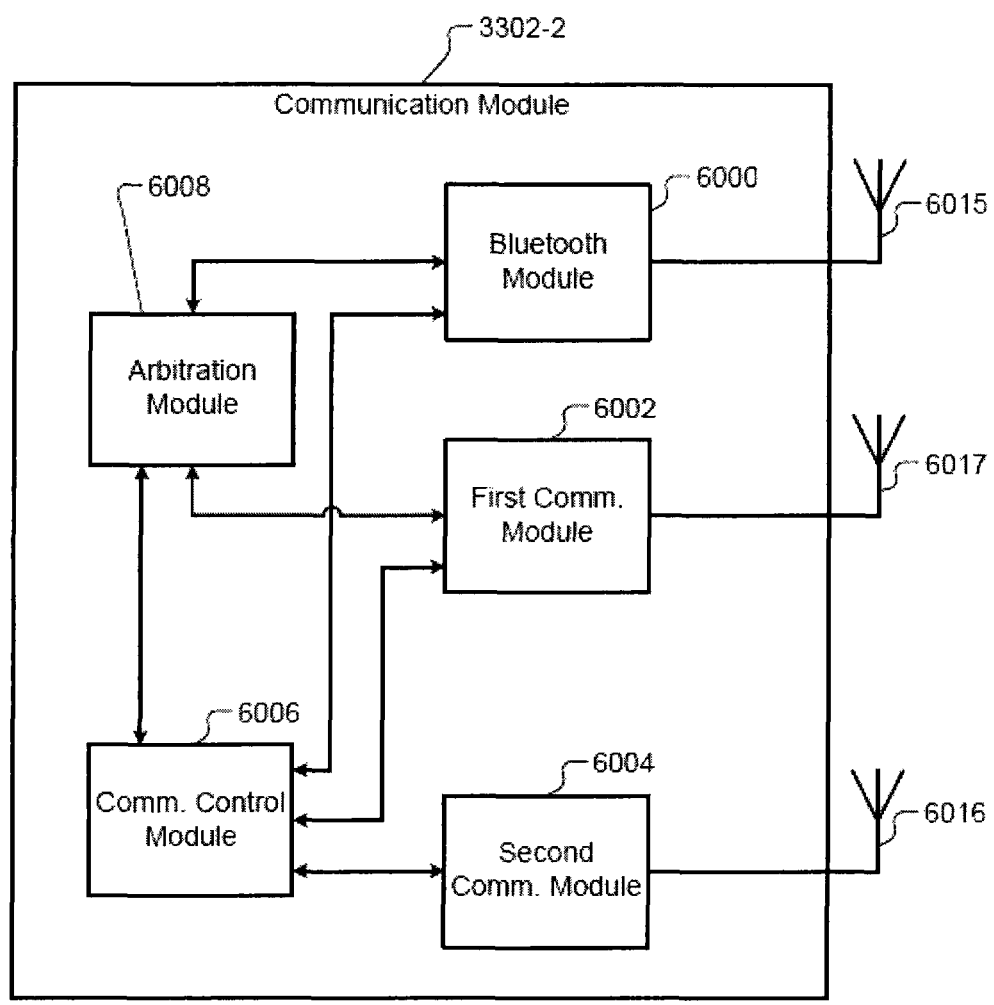
FIG. 20B is a functional block diagram of a communication module used by the diabetes manager of FIG. 12, where the communication module does not use a shared antenna.

Referring now to FIGS. 20A and 20B, different implementations of the communication module 3302 are shown. In FIG. 20A, a communication module 3302-1 comprises a Bluetooth module 6000, a first communication module 6002, a second communication module 6004, a communication control module 6006, an arbitration module 6008, and an antenna switching module 6010. The Bluetooth module 6000 and the first communication module 6002 are integrated into an integrated circuit (IC) 6012. The Bluetooth module 6000 and the first communication module 6002 communicate in a 2.4 GHz frequency band (industrial, scientific, and medical or ISM band). The Bluetooth module 6000 and the first communication module 6002 share a first antenna 6014. The second communication module 6004 may operate in the same ISM band or in a different frequency band and uses a second antenna 6016. The first and second antennas 6014 and 6016 are spatially orthogonal to reduce interference.

In FIG. 20B, a communication module 3302-2 comprises the Bluetooth module 6000, the first communication module 6002, the second communication module 6004, the communication control module 6006, and the arbitration module 6008. The Bluetooth module 6000 and the first communication module 6002 are not integrated into an IC. Additionally, the Bluetooth module 6000 and the first communication module 6002 have separate antennas 6015 and 6017, respectively. Accordingly, the antenna switching module 6010 is unnecessary. The antennas 6015, 6016, and 6017 are spatially orthogonal to reduce interference. The following discussion uses the implementation shown in FIG. 20A as an example only. The teachings disclosed below (except those related to sharing an antenna) apply equally to the implementation shown in FIG. 20B.

In FIG. 20A, the Bluetooth module 6000 communicates with the insulin pump 2914 and the PC 2906. The first communication module 6002 communicates with the CGM 2910 using the Gazell protocol. The first communication module 6002 estimates blood glucose based on the data received from the CGM 2910. The second communication module 6004 communicates with other device 6018 using a wireless communication protocol different than Bluetooth and Gazell protocols. For example, the second communication module 6004 may use a communication protocol suitable for communicating with a Medingo insulin pump. Alternatively, the second communication module 6004 may use WiFi, Machine-to-Machine cellular, Worldwide Interoperability for Microwave Access (WiMAX), or other wireless or wireline communication protocols developed by IEEE or other entities.

Throughout the present disclosure, the insulin pump 2914, the PC 2906, and the CGM 2910 are used as exemplary devices. Further, the discussion related to priorities of the insulin pump 2914, the PC 2906, and the CGM 2910 is for example only. Additionally or alternatively, the Bluetooth module 6000 and the first communication module 6002 can communicate with several other devices having different priorities.

Several techniques can be used to manage coexistence of the Bluetooth module 6000 and the first communication module 6002, which utilize the Bluetooth and Gazell protocols, respectively. For example, the techniques can include application-level control, frequency mapping, and/or hardware control of transceivers used in the Bluetooth module 6000 and the first communication module 6002. These techniques decrease probability of collisions and interference between communications performed by the Bluetooth module 6000 and the first communication module 6002. Application-level control includes utilizing the user interfaces 3306 to avoid simultaneous communication using the Bluetooth module 6000 and the first communication module 6002. For example, the patient 2900 can utilize the user interfaces 3306 to manually select one device to interact with at a time. Frequency mapping includes allocating distinct channels within the ISM band to the Bluetooth module 6000 and the first communication module 6002. The communication control module 6006 performs the frequency mapping as explained below.

Hardware control of transceivers involves using a RF coexistence interface such as BL6450 developed by Texas Instruments that provides RF coexistence signals that can be adapted for use with the Bluetooth module 6000 and the first communication module 6002. For example, Bluetooth asynchronous connectionless link (ACL) packets and Gazell protocol packets transmitted/received by the Bluetooth module 6000 and the first communication module 6002 can be interleaved in a controlled manner. The result is an application that appears as communicating via the Bluetooth module 6000 and the first communication module 6002 simultaneously. The communication control module 6006 and the arbitration module 6008 control the transceivers of the Bluetooth module 6000 and the first communication module 6002 as explained below. In addition, the arbitration module 6008 can manage the coexistence by automatically arbitrating priority between the Bluetooth module 6000 and the first communication module 6002 based on various considerations as explained below.

The communication control module 6006 controls communication of the diabetes manager 2904 with the other devices in the diabetes management system 2390 via the Bluetooth module 6000 and the first and second communication modules 6002 and 6004. The arbitration module 6008 arbitrates priority between the Bluetooth module 6000 and the first communication module 6002 when communication via the Bluetooth module 6000 and the first communication module 6002 is attempted concurrently. The antenna switching module 6010 switches the connection of the first antenna 6014 between the Bluetooth module 6000 and the first communication module 6002 depending on whether the Bluetooth module 6000 or the first communication module 6002 is granted priority.

More specifically, the Bluetooth module 6000 selectively communicates in the ISM band with the insulin pump 2914 external to the diabetes manager 2904 via the first antenna 6014 using the Bluetooth protocol. The first communication module 6002 selectively communicates in the ISM band with the CGM 2910 external to the diabetes manager 2904 via the first antenna 6014 using the Gazell protocol. To minimize interference and number of packet retries, the communication control module 6006 allocates a first channel in the ISM band to the Bluetooth module 6000 and allocates a second channel in the ISM band to the first communication module 6002. For example, the communication control module 6006 can use frequency mapping, where channels allocated to first communication module 6002 are removed from Bluetooth channel map. Further, the communication control module 6006 reduces interference using techniques including time division multiple access (TDMA), channel hopping, channel adaptation, etc.

The arbitration module 6008 arbitrates priority between the Bluetooth module 6000 and the first communication module 6002 in many ways. For example, the arbitration module 6008 typically grants permission to communicate to the Bluetooth module 6000 and denies permission to communicate to the first communication module 6002 when the Bluetooth module 6000 and the first communication module 6002 request permission to communicate concurrently. This is because the insulin pump 2914 delivers therapy (insulin) to the patient 2900 and therefore generally takes precedence over the CGM 2910, which collects diagnostic data for estimating glucose level of the patient 2900. Additionally, while the diagnostic data can be read from the CGM 2910 periodically, scheduled delivery of insulin generally cannot be delayed.

The arbitration module 6008 allocates priority differently when a device other than the insulin pump 2914 (e.g., the PC 2906) is contending with the CGM 2910 for priority to communicate with the diabetes manager 2904. For example, when the Bluetooth module 6000 requests permission to communicate with the PC 2906 and the first communication module 6002 also requests permission to communicate concurrently, the arbitration module 6008 denies permission to communicate to the Bluetooth module 6000 and grants permission to communicate to the first communication module 6002.

Occasionally, the diagnostic data may indicate that the glucose level of the patient 2900 is less than a predetermined threshold, while the insulin pump 2914 may be programmed to deliver a bolus insulin dose to the patient 2900. In such a situation, communicating the diagnostic data collected by the CGM 2910 to the diabetes manager 2904 takes precedence over communicating with the insulin pump 2914. Accordingly, the arbitration module 6008 denies permission to communicate to the Bluetooth module 6000 and grants permission to communicate to the first communication module 6002 when the Bluetooth module 6000 and the first communication module 6002 request permission to communicate concurrently.

Stated generally, a handheld medical device (e.g., the diabetes manager 2904) comprises a first communication module (e.g., the Bluetooth module 6000) that selectively communicates in a first frequency band (e.g., the ISM band) with a first device (e.g., the insulin pump 2914) external to the handheld medical device via a first antenna (e.g., 6014) using a first wireless communication protocol (e.g., Bluetooth). The first device administers a substance (e.g., insulin) to a patient (2900) by communicating with the handheld medical device via the first communication module. A second communication module (e.g., 6002) selectively communicates in the first frequency band with a second device (e.g., the CGM 2910) external to the handheld medical device via the first antenna using a second wireless communication protocol (e.g., Gazell). The second device monitors a health parameter (e.g., blood glucose level) of the patient by communicating with the handheld medical device via the second communication module. An arbitration module (e.g., 6008) grants permission to communicate to the first communication module and denies permission to communicate to the second communication module when the first and second communication modules request permission to communicate concurrently and when the first device has a higher priority than the second device based on a condition of the patient. In some implementations, the first communication module (e.g., the Bluetooth module 6000) and the second communication module (e.g., 6002) use separate antennas.

Further, the handheld medical device comprises an antenna switching module (e.g., 6010) that connects the first antenna to the first communication module when the first communication module is granted permission to communicate and that connects the first antenna to the second communication module when the second communication module is granted permission to communicate. Additionally, the handheld medical device comprises a third communication module (e.g., 6004) that selectively communicates in a second frequency band with a third device (e.g., the other device 6018) external to the handheld medical device via a second antenna (e.g., 6016) using a third wireless communication protocol (e.g., WiFi, WiMAX, etc.) that is different than the first and second wireless communication protocols.

The arbitration module 6008 can arbitrate priority based on other events, conditions, and operations of the diabetes manager 2904. For example, the arbitration module 6008 can deny priority to at least one of the Bluetooth module 6000 and the first communication module 6002 when the BGM module 3300 performs blood glucose measurements. In some implementations, the communication control module 6006 may disable communication of the Bluetooth module 6000 and the first and second communication modules 6002 and 6004 when the BGM module 3300 performs blood glucose measurements. This is because these communications can cause electrical interference in glucose sensing circuitry of the BGM module 3300, which can render the blood glucose measurements inaccurate. Additionally or alternatively, these communications can increase internal temperature of the diabetes manager 2904, which can also render the blood glucose measurements inaccurate.

Further, the CGM 2910 and/or the insulin pump 2914 may generate alarms or alerts to indicate predetermined conditions. For example, the CGM 2910 may indicate when glucose level of the patient 2900 is less than a predetermined threshold. The insulin pump 2914 may indicate when insulin supply in the insulin pump 2914 is less than a predetermined threshold, and so on. The arbitration module 6008 may grant priority to the communication module corresponding to the device generating the alarm or alert. Occasionally, the patient 2900 may press a key on the user interface 3306 to send a message via the mobile device 2932 indicating an emergency condition. Accordingly, the arbitration module 6008 may grant priority to the Bluetooth module 6000 to communicate with the mobile device 2932.

Additionally, the arbitration module 6008 may grant or deny priority based on a state of charge of the battery. For example, when the state of charge is less than a predetermined threshold, the arbitration module 6008 may grant priority to the Bluetooth module 6000 to communicate with the insulin pump 2914 and may deny priority to the first communication module 6002, which communicates with the CGM 2910.

The arbitration module 6008 can also arbitrate priority based on the direction of communication between the diabetes manager 2904 and the insulin pump 2914, the CGM 2910, and the PC 2906. For example, when the arbitration module 6008 receives signals from the Bluetooth module 6000 and the first communication module 6002 for concurrent communication, the arbitration module 6008 identifies the insulin pump 2914, the PC 2906, or the CGM 2910 as the source or destination of the signals. Depending on the operation being performed, the arbitration module 6008 determines whether the insulin pump 2914, the PC 2906, or the CGM 2910 has a higher priority and grants permission to communicate to the corresponding communication module. For example, when the diabetes manager 2904 receives configuration or other updates (e.g., firmware updates) from the PC 2906, the arbitration module 6008 grants priority to the Bluetooth module 6000 and denies priority to the first communication module 6002.

Figure 21:
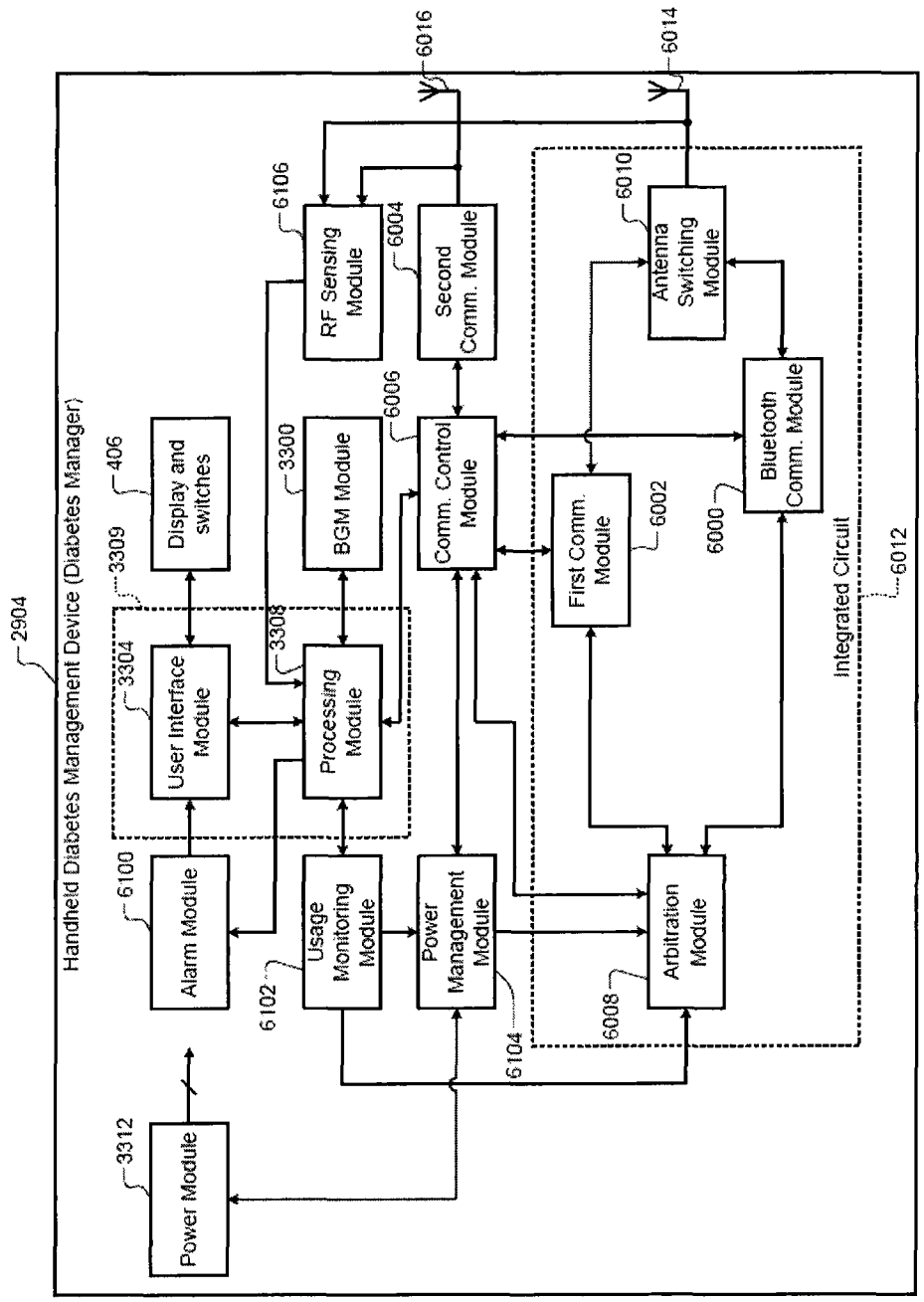
FIG. 21 is a detailed functional block diagram of the diabetes manager of FIG. 12.

Referring now to FIG. 21, a detailed functional block diagram of the diabetes manager 2904 is shown. Although the Bluetooth module 6000 and the first communication module 6002 are shown integrated and sharing the first antenna 6014, the Bluetooth module 6000 and the first communication module 6002 need to not be integrated and can have separate antennas as shown in FIG. 20B. Elements of the diabetes manager 2904 that are described above are not described again. In addition to these elements, the diabetes manager 2904 includes an alarm module 6100, a usage monitoring module 6102, a power management module 6104, and a radio frequency (RF) sensing module 6106.

The alarm module 6100 outputs alarm signals (e.g., audio, video, vibrate, and/or other signals) to the user interfaces 3306 (e.g., when blood glucose level is less than a first predetermined threshold or greater than a second predetermined threshold). The usage monitoring module 6102 monitors usage of the diabetes manager 2904. For example, the usage monitoring module 6102 detects when the diabetes manager 2904 is idle, generating an alarm, measuring blood glucose level, or communicating with the PC 2906, the insulin pump 2914, the CGM 2910, and so on.

The power management module 6104 monitors the amount of power available from the battery. Based on the usage of the diabetes manager 2904 and the power available from the battery, the power management module 6104 deactivates one or more components of the diabetes manager 2904 to save power. Deactivation of a component includes supplying no power to the component (i.e., shutting down the component) or supplying minimum power to put the component in a standby or power save mode (e.g., turning off or slowing one or more clocks used by the component).

Based on the usage and the power available, the arbitration module 6008 arbitrates priority between the Bluetooth module 6000 and the first communication module 6002. For example, when the power available is less than a predetermined threshold, the arbitration module 6008 can deny permission to the communication module that will consume more power and grant priority to the communication module that will consume less power.

When the BGM module 3300 measures blood glucose level in the blood sample, the power management module 6104 deactivates at least one or all of the Bluetooth module 6000 and the first and second communication modules 6002 and 6004. The RF sensing module 6106 senses RF signals in the proximity of the diabetes manager 2904. For example, the RF sensing module 6106 uses techniques such as clear channel assessment (CCA), which is generally used to find a best channel for transmission, to sense RF signals. Specifically, rather than using CCA to find the best channel for transmission, the RF sensing module 6106 uses CCA to detect RF emitting devices in the vicinity of the diabetes manager 2904. The processing module 3308 deactivates the BGM module 3300 when the RF sensing module 6106 senses the RF signals proximate to the diabetes manager 2904 to avoid interference with the blood glucose measurement.

In some implementations, the RF sensing module 6106 can be implemented in transceivers of the Bluetooth module 6000 and the first and second communication modules 6002 and 6004. For example, the transceivers include radio signal strength indicator (RSSI) circuitry that determines an amount of power needed to maintain a communications link with a device. The RSSI circuitry of the transceivers can be used to scan the respective frequency bands to detect RF signals proximate to the diabetes manager 2904.

Figure 22:
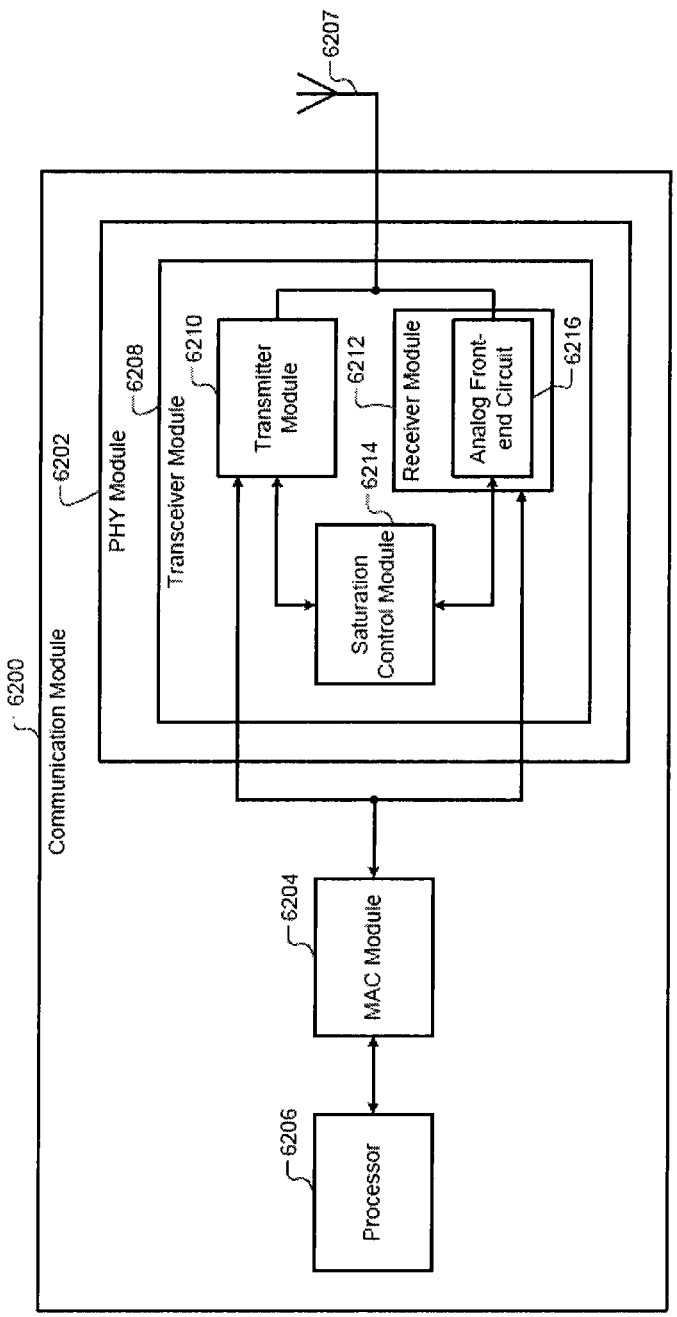
FIG. 22 is a functional block diagram of a communication module.

Referring now to FIG. 22, a functional block diagram of a communication module 6200 is shown. The communication module 6200 is representative of the Bluetooth module 6000 or the first or second communication module 6002 or 6004. The communication module 6200 comprises a physical layer (PHY) module 6202, a media access control (MAC) module 6204, a processor module 6206, and an antenna 6207. The PHY module 6202 comprises a transceiver module 6208, which includes a transmitter module 6210, a receiver module 6212, and a saturation control module 6214. The transmitter module 6210 is collocated with the receiver module 6212. The transmitter module 6210 and the receiver module 6212 transmit and receive data via the antenna 6207, respectively. For example, for the first communication module 6002, the transceiver module 6208 may include an nRF24LE1 transceiver developed by Nordic Semiconductor, Inc. described in the nRF24LE1 Ultra-low Power Wireless System On-Chip Solution, Product Specification v1.4, which is incorporated herein by reference in its entirety.

The MAC module 6204 communicates with the transmitter module 6210 and the receiver module 6212 and controls access of the communication module 6200 to the wireless medium. The processor module 6206 processes data transmitted and received by the transmitter module 6210 and the receiver module 6212, respectively. The receiver module 6212 includes a front-end circuit 6216 that performs functions including demodulation, analog-to-digital conversion (ADC), automatic gain control (AGC), etc. The saturation control module 6214 prevents saturation of the front-end circuit 6216 by the transmitter module 6210 to minimize interference. In some implementations, the AGC in the front-end circuit 6216 can prevent saturation of the front-end circuit 6216 so long as signal strengths of received signals are less than a predetermined threshold.

Figure 23:
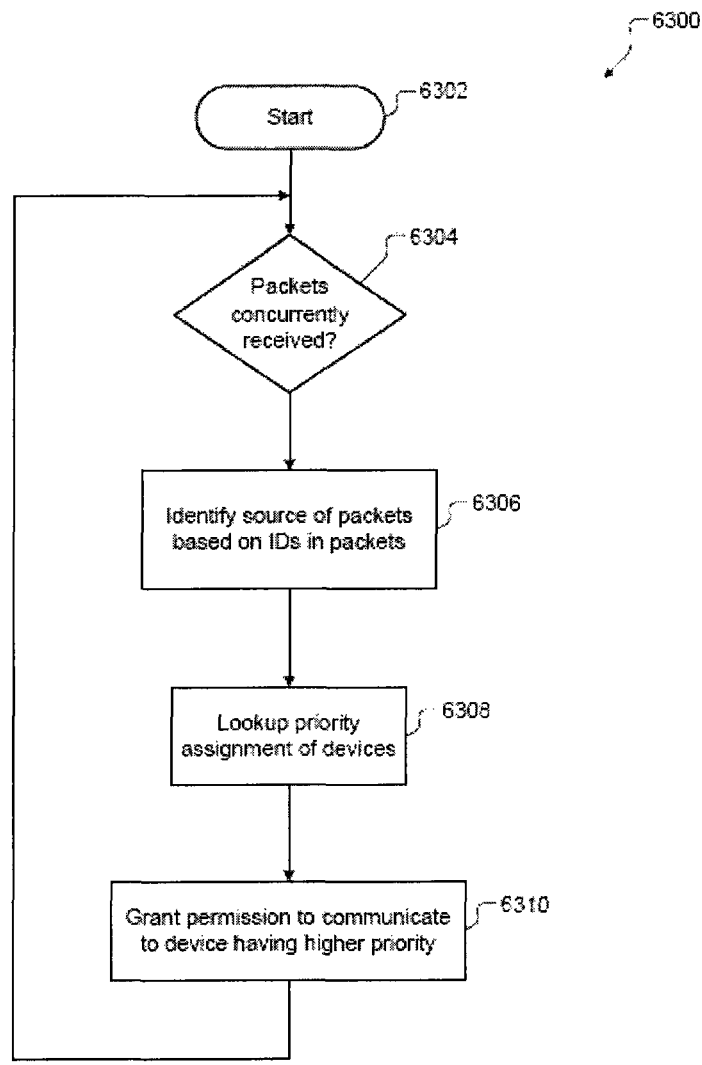
FIG. 23 is a flowchart of a method for arbitrating priority between a plurality of communication modules using a shared antenna.

Referring now to FIG. 23, in an exemplary implementation, the arbitration module 6008 performs a method 6300 for arbitrating priority between the Bluetooth module 6000 and the first communication module 6002. Control begins at 6302. At 6304, control determines if requests for simultaneous communication are received from the Bluetooth module 6000 and the first communication module 6002. For example, packets may be simultaneously received via the first and second antennas 6014 and 6016. If the result at 6304 is false, control waits. If the result at 6304 is true, at 6306, control identifies devices that originated the packets based on identifying information included in the packets.

At 6308, control looks up predetermined priorities for the identified devices. For example, the predetermined priorities may be stored in a lookup table or control registers in the arbitration module 6008. The predetermined priorities can be altered/updated dynamically based on the usage and operation of the diabetes manager 2904 and associated devices described above. At 6310, based on the priority assigned to the identified devices, control grants permission to communicate to the device having higher priority. Control returns to 6302.

In an exemplary embodiment, the arbitration module 6008 arbitrates priority between the Bluetooth module 6000 and the first communication module 6002 using coexistence signals as follows. For managing coexistence, the Bluetooth module 6000 of FIG. 5 utilizes three coexistence signals: BT_RF_ACTIVE, BT_PRIORITY, and BT_TX_CONFX. The Bluetooth module 6000 outputs BT_RF_ACTIVE to indicate transmit or receive activity of the Bluetooth module 6000. The Bluetooth module 6000 outputs BT_PRIORITY to indicate that a priority transaction is about to occur and whether the activity is transmit or receive type. BT_TX_CONFX is an input to the Bluetooth module 6000 that disables an internal power amplifier of the Bluetooth module 6000 when asserted.

The first communication module 6002 utilizing the nRF24LE1 transceiver does not inherently include hardware to implement the co-existence signals. Similar operations, however, can be performed by the first communication module 6002 using the arbitration module 6008 and/or the communication control module 6006. For example, when the first communication module 6002 is about to receive diagnostic data from the CGM 2910, the arbitration module 6008 and/or the communication control module 6006 can assert BT_TX_CONFX, check BT_RF_ACTIVE to ensure that the Bluetooth module 6000 is no longer active, and allow the first communication module 6002 to receive the diagnostic data from the CGM 2910. After the transaction between first communication module 6002 and the CGM 2910 is completed, the arbitration module 6008 and/or the communication control module 6006 can de-assert BT_TX_CONFX. An exemplary method for managing coexistence using this approach performed by the arbitration module 6008 and/or the communication control module 6006 is explained below.

Figure 24:
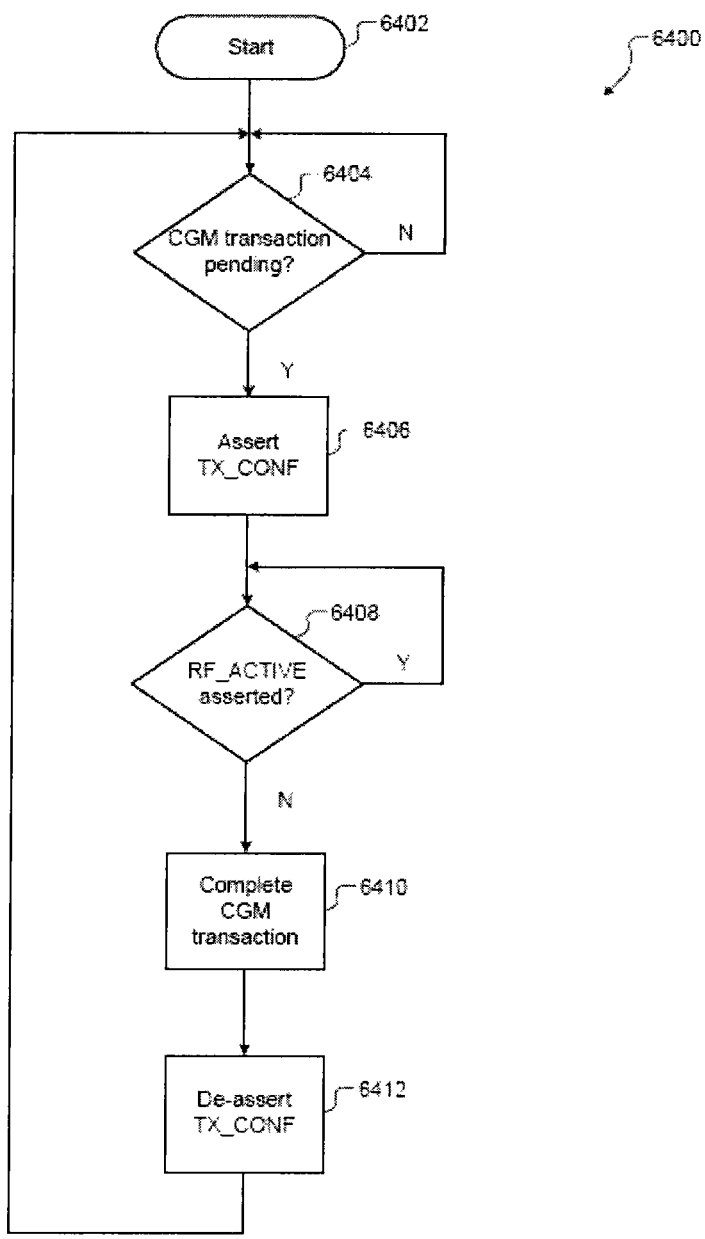
FIG. 24 is a flowchart of a method for managing coexistence of a plurality of communication modules using a shared antenna.

Referring now to FIG. 24, a flowchart of a method 6400 for managing coexistence of the Bluetooth module 6000 and the first communication module 6002 using a shared antenna is shown. Control begins at 6402. At 6404, control determines if a transaction with CGM 2910 using the first communication module 6002 is pending. Control waits if a transaction is not pending. At 6406, if a transaction is pending, control asserts BT_TX_CONF, which disables an internal power amplifier of the Bluetooth module 6000. At 6408, control determines if BT_RF_ACTIVE is asserted, which indicates transmit or receive activity of the Bluetooth module 6000. Control returns to 6408 if BT_RF_ACTIVE is asserted. At 6410, if BT_RF_ACTIVE is not asserted, which indicates no transmit or receive activity by the Bluetooth module 6000, control completes the pending transaction using the first communication module 6002. At 6412, control de-asserts BT_TX_CONF, which enables an internal power amplifier of the Bluetooth module 6000, and control returns to 6402.

When large amounts of diagnostic data are downloaded from the CGM 2910 using the first communication module 6002, the RF usage may have large gaps where the Bluetooth module 6000 can have an opportunity to send and receive packets. For example, a largest Gazell packet may be 1.316 msec long. Accordingly, even if 10 records were downloaded at a time, for example, including acknowledgements, the Bluetooth module 6000 may be disabled on the order of 15 to 30 msec depending on the number of retries and other timing parameters.

Further, when a large number of records are to be downloaded from the CGM 2910, the number of records can be divided into groups with a gap of 50 to 100 msec between the groups due to other system constraints. The quality of service (QoS) of the Bluetooth module 6000 is set to reliable so that Bluetooth packets are retried until Bluetooth link breaks down, which makes the Bluetooth interface robust. The default link timeout for the Bluetooth interface is typically 20 seconds while applications generally have a much shorter timeout such as 1 second.

A sniff interval setting of the Bluetooth module 6000 can impact this strategy. While Bluetooth is a polling-based system, the connection between the diabetes manager 2904 and the insulin pump 2914 can use sniff mode to save power. The sniff interval can be set to 16 msec, for example, which means that the slave and host devices (e.g., the insulin pump 2914 and the Bluetooth module 6000) can wake up to exchange packets every 16 msec.

In summary, if the first communication module 6002 allows the Bluetooth module 6000 to complete transactions and does not disable the Bluetooth module 6000 for an extended period of time, an RF coexistence interface such as BL6450 provided by Texas Instruments can be used to manage coexistence of the Bluetooth module 6000 and the first communication module 6002.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A handheld diabetes management device that arbitrates priority among multiple communication modules having a shared antenna for communicating with a plurality of medical devices, the handheld diabetes management device comprising:
   a blood glucose measuring module that selectively measures blood glucose in a blood sample;
   a first communication module that selectively communicates in a first frequency band with an insulin infusion pump external to the handheld diabetes management device via a first antenna using a first wireless communication protocol;
   a second communication module that selectively communicates in the first frequency band with a continuous glucose monitor external to the handheld diabetes management device via the first antenna using a second wireless communication protocol;
   an arbitration module that receives signals from the first and second communication modules for concurrent communication with the insulin infusion pump and the continuous glucose monitor, respectively, identifies the insulin infusion pump and the continuous glucose monitor as the source or destination of the signals, determines that the insulin infusion pump has a higher priority than the continuous glucose monitor, and grants permission to communicate to the first communication module, and denies permission to communicate to the second communication module; and
   a third communication module that selectively communicates in a second frequency band with a device external to the handheld diabetes management device via a second antenna using a third wireless communication protocol that is different than the first and second wireless communication protocols, wherein the second frequency band is different than the first frequency band, wherein the device is different than the insulin infusion pump and the continuous glucose monitor, and wherein the first and second antennas are orthogonal.

2. The handheld diabetes management device of claim 1 further comprising:
   a power management module that deactivates the first and second communication modules when the blood glucose measuring module measures the blood glucose in the blood sample;
   a radio frequency (RF) sensing module that selectively senses RF signals; and
   a processing module that deactivates the blood glucose measuring module when the RF sensing module senses the RF signals proximate to the handheld diabetes management device.

3. The handheld diabetes management device of claim 1 further comprising a communication control module that allocates a first channel set in the first frequency band to the first communication module and that allocates a second channel set in the first frequency band to the second communication module.

4. The handheld diabetes management device of claim 1 further comprising an antenna switching module that connects the first antenna to the first communication module when the first communication module is granted permission to communicate and that connects the first antenna to the second communication module when the second communication module is granted permission to communicate.

5. The handheld diabetes management device of claim 1 further comprising a communication control module that
   detects when a communication of the second communication module is pending,
   disables a power amplifier of the first communication module,
   confirms that the first communication module has stopped communication,
   allows the second communication module to complete the communication, and
   enables the power amplifier of the first communication module.

6. A handheld medical device that arbitrates priority among multiple communication modules having a shared antenna for communicating with a plurality of medical devices, the handheld medical device comprising:
   a blood glucose measuring mode that selectively measures blood glucose in a blood sample;
   a first communication module that selectively communicates in a first frequency band with a first device external to the handheld medical device via a first antenna using a first wireless communication protocol, wherein the first device administers a substance to a patient by communicating with the handheld medical device via the first communication module,
   a second communication module that selectively communicates in the first frequency band with a second device external to the handheld medical device via the first antenna using a second wireless communication protocol, wherein the second device monitors a health parameter of the patient by communicating with the handheld medical device via the second communication module;

an arbitration module that grants permission to communicate to the first communication module and that denies permission to communicate to the second communication module when the first and second communication modules request permission to communicate concurrently and when the first device has a higher priority than the second device based on a condition of the patient; and a communication control module that detects when a communication of the second communication module is pending, disables a power amplifier of the first communication module, confirms that the first communication module has stopped communication, allows the second communication module to complete the communication, and enables the power amplifier of the first communication module.

7. The handheld medical device of claim 6 further comprising:

a power management module that deactivates the first and second communication modules when the blood glucose measuring module measures the blood glucose in the blood sample;

a radio frequency (RF) sensing module that selectively senses RF signals; and a processing module that deactivates the blood glucose measuring module when the RF sensing module senses the RF signals proximate to the handheld medical device.

8. The handheld medical device of claim 6 further comprising:

a third communication module that selectively communicates in a second frequency band with a third device external to the handheld medical device via a second antenna using a third wireless communication protocol that is different than the first and second wireless communication protocols, wherein the second frequency band is different than the first frequency band, and wherein the first and second antennas are orthogonal to reduce near-field interference.

9. The handheld medical device of claim 6 further comprising a communication control module that allocates a first channel set in the first frequency band to the first communication module and that allocates a second channel set in the first frequency band to the second communication module.

10. The handheld medical device of claim 6 further comprising an antenna switching module that connects the first antenna to the first communication module when the first communication module is granted permission to communicate and that connects the first antenna to the second communication module when the second communication module is granted permission to communicate.

11. A handheld diabetes management device that arbitrates priority among multiple communication modules having a shared antenna for communicating with a plurality of medical devices, the handheld diabetes management device comprising:

a blood glucose measuring module that selectively measures blood glucose in a blood sample;

a first communication module that selectively communicates in a first frequency band with an insulin infusion pump external to the handheld diabetes management device via a first antenna using a first wireless communication protocol, wherein the insulin infusion pump selectively receives an instruction from the handheld diabetes management device to administer insulin to a patient;

a second communication module that selectively communicates in the first frequency band with a continuous glucose monitor external to the handheld diabetes management device via the first antenna using a second wireless communication protocol, wherein the continuous glucose monitor selectively communicates a glucose level of the patient to the handheld diabetes management device;

an arbitration module that denies permission to communicate to the first communication module and that grants permission to communicate to the second communication module when the first and second communication modules request permission to communicate concurrently and when the blood glucose level of the patient is less than a threshold;

a collection application implemented as computer executable instructions in the data store of the diabetes care manager, the collection application executes a structured collection procedure for obtaining measurement data from the meter and provides access to the measurement data, wherein the structured collection procedure having parameters including a schedule of collection events;

a configuration application implemented as computer executable instructions in the data store of the diabetes care manager that accesses and manipulates the parameters of the structured collection procedure using a set of action commands, wherein the set of action commands are defined in compliance with the communication protocol; and a collection interface implemented as computer executable instructions in the data store of the diabetes care manager that receives an action command from the configuration application, executes the received action command and issues a response command in response thereto, wherein the response command is defined in compliance with the communication protocol.

12. The handheld diabetes management device of claim 11 further comprising:

a power management module that deactivates the first and second communication modules when the blood glucose measuring module measures the blood glucose in the blood sample;

a radio frequency (RF) sensing module that selectively senses RF signals; and a processing module that deactivates the blood glucose measuring module when the RF sensing module senses the RF signals proximate to the handheld diabetes management device.

13. The handheld diabetes management device of claim 11 further comprising:

a third communication module that selectively communicates in a second frequency band with a device external to the handheld diabetes management device via a second antenna using a third wireless communication protocol that is different than the first and second wireless communication protocols, wherein the second frequency band is different than the first frequency band, wherein the device is different than the insulin infusion pump and the continuous glucose monitor, and wherein the first and second antennas are orthogonal.

14. The handheld diabetes management device of claim 11 further comprising a communication control module that allocates a first channel set in the first frequency band to the first communication module and that allocates a second channel set in the first frequency band to the second communication module.

15. The handheld diabetes management device of claim 11 further comprising an antenna switching module that connects the first antenna to the first communication module when the first communication module is granted permission to communicate and that connects the first antenna to the second communication module when the second communication module is granted permission to communicate.

16. The handheld diabetes management device of claim 11 further comprising a communication control module that
- detects when a communication of the second communication module is pending,
- disables a power amplifier of the first communication module,
- confirms that the first communication module has stopped communication,
- allows the second communication module to complete the communication, and
- enables the power amplifier of the first communication module.

* * * * *